(12) United States Patent
Currie et al.

(10) Patent No.: US 7,160,885 B2
(45) Date of Patent: Jan. 9, 2007

(54) CERTAIN 6, 8-(HETEROARYL OR ARYL) DISUBSTITUTED IMIDAZO[1,2-A]PYRAZINES AS MODULATORS OF HSP90 COMPLEX ACTIVITY

(75) Inventors: Kevin S. Currie, North Branford, CT (US); Robert W. DeSimone, Durham, CT (US); Douglas A. Pippin, Branford, CT (US); James W. Darrow, Wallingford, CT (US); Scott A. Mitchell, East Haven, CT (US)

(73) Assignee: CGI Pharmaceuticals, Inc., Branford, CT (US)

( * ) Notice: Subject to any disclaimer, the term of this patent is extended or adjusted under 35 U.S.C. 154(b) by 292 days.

(21) Appl. No.: 10/776,631

(22) Filed: Feb. 10, 2004

(65) Prior Publication Data

US 2005/0054649 A1     Mar. 10, 2005

Related U.S. Application Data

(60) Provisional application No. 60/446,379, filed on Feb. 10, 2003.

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| C07D 471/00 | (2006.01) |

(52) U.S. Cl. ..................... 514/249; 544/350
(58) Field of Classification Search ............ None
See application file for complete search history.

(56) References Cited

U.S. PATENT DOCUMENTS

| | | | |
|---|---|---|---|
| 5,593,997 | A | 1/1997 | Dow et al. |
| 5,658,857 | A | 8/1997 | Andree et al. |
| 5,783,576 | A | 7/1998 | Roos et al. |
| 6,919,341 | B1 | 7/2005 | Paruch et al. |
| 2003/0212073 | A1 | 11/2003 | Currie et al. |
| 2004/0063715 | A1 | 4/2004 | Paruch et al. |

(Continued)

FOREIGN PATENT DOCUMENTS

| | | |
|---|---|---|
| DE | 43 37 609 A1 | 5/1995 |
| EP | 0 480 713 | 4/1992 |

(Continued)

OTHER PUBLICATIONS

Jeffery, Trina K., et al., "Phosphodiesterase III and V Inhibitors on Pulmonary Artery from Pulmonary Hypertensive Rats: Differences Between Early and Established Pulmonary Hypertension" Journal of Cardivascular Pharmacology 1998, vol. 32, No. 2, pp. 213-219.

(Continued)

Primary Examiner—Zachary C. Tucker
(74) Attorney, Agent, or Firm—Finnegan, Henderson, Farabow, Garrett & Dunner, LLP

(57) ABSTRACT

This invention pertains to compounds of Formula I:

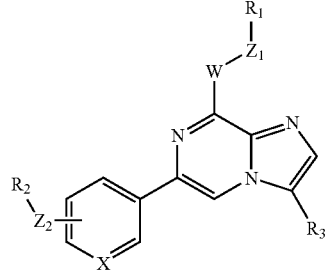

(Formula I)

and the pharmaceutically-acceptable forms thereof.

The variables $R_1$, $R_2$, $R_3$, $Z_1$, $Z_2$, W, and X shown in Formula I are defined herein.

The invention also provides pharmaceutical compositions containing one or more compound of Formula I, or pharmaceutically acceptable form of such compounds, and one or more pharmaceutically acceptable carriers, excipients, or diluents.

The invention further comprises methods of treating patients suffering from certain diseases and disorders responsive to Hsp90 complex modulation, which comprise administering to such patients an amount of a compound of Formula I effective to reduce signs or symptoms of the disease or disorder. These diseases include cancer, including chronic myeloid leukemia, melanoma, breast, ovarian, brain, thyroid, colorectal, prostate, and bladder cancer, heart disease, stroke, autoimmune/inflammatory diseases, and neurodegenerative diseases. Thus methods of treatment include administering a sufficient amount of a compound of Formula I or form thereof to decrease the symptoms or slow the progression of these diseases or disorders.

The invention also encompasses methods of treating non-human patients, including livestock and domesticated companion animals, suffering from a disease or disorder responsive to Hsp90 complex modulation.

Methods of treatment include administering a compound of Formula I as a single active agent or administering a compound of Formula I in combination with one or more other therapeutic agent.

The invention also includes a method for determining the presence of certain kinases or Hsp90 complex in a sample, comprising contacting the sample with a compound of Formula I or form thereof, and detecting Hsp9O complex activity in the sample.

41 Claims, No Drawings

U.S. PATENT DOCUMENTS

| | | |
|---|---|---|
| 2004/0067951 A1 | 4/2004 | DeSimone et al. |
| 2004/0072835 A1 | 4/2004 | Paruch et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |

FOREIGN PATENT DOCUMENTS

| | | |
|---|---|---|
| WO | WO 88/04298 | 6/1988 |
| WO | WO 95/12594 | 5/1995 |
| WO | WO 96/04298 | 2/1996 |
| WO | WO 96/34866 | 11/1996 |
| WO | WO 99/28322 | 6/1999 |
| WO | WO 01/27119 A2 | 4/2001 |
| WO | WO 02/10170 A1 | 2/2002 |
| WO | WO 02/30428 A1 | 4/2002 |
| WO | WO 02/060492 A1 | 8/2002 |
| WO | WO 02/066481 | 8/2002 |
| WO | WO 02/076985 | 10/2002 |
| WO | WO 03/070732 | 8/2003 |
| WO | WO 2003/089434 | 10/2003 |
| WO | WO 2004/022562 | 3/2004 |
| WO | WO 2004/026310 | 4/2004 |
| WO | WO 2004/026877 | 4/2004 |
| WO | WO 2004/072080 | 8/2004 |
| WO | WO 2004/072081 | 8/2004 |
| WO | WO 2005/005429 | 1/2005 |
| WO | WO 2005/014599 | 2/2005 |
| WO | WO 2005/019220 | 3/2005 |
| WO | WO 2005/047290 | 5/2005 |

OTHER PUBLICATIONS

Hanks, Steven K., "Hanks Classification" 1994, pp. 1-4 http://pkr.sdsc.edu/html/pk_catalytic/pk_hanks_class.html.

Lumma, William C., et al., "Piperazinylimidazo }1,2-alpyrazines with Selective Affinity for in Vitro_-Adrenergic Receptor Subtypes" J. Med. Chem. 1983, vol. 26, pp. 357-363.

Stenberg, Kaj A. E., et al., "KinMutBase, a database of human disease-causing protein kinase mutations" Nucleic Acids Research 2000, vol. 28, pp. 369-372.

Vitse, O. et al., "New Imidazo[1,2-a]pyrazine Derivatives with Bronchodilatory and Cyclic Nucleotide Phosphodiesterase Inhibitory Activities" Bioorganic & Medicinal Chemistry 1999, vol. 7, pp. 1059-1065.

Ding et al. (2002) "A Combinatorial Scaffold Approach toward Kinase-Directed Heterocycle Libraries," J. Am. Chem. Soc., 124(8): 1594-1596.

"Protein Kinases in Disease," references produced from a Sep. 24, 1997, search of the On-line Meddelian Inheritance in Man (OMIM) database, pp. 1-11, from http://bioinformatics.weizmann.ac.il/Kinases/pkr/pk_medicine.html.

International Search Report dated Oct. 22, 2003, for Application No. PCT/US03/12222, International filing date Apr. 21, 2003.

Written Opinion dated Dec. 5, 2003, for Application No. PCT/US03/12222, International filing date Apr. 21, 2003.

Second Written Opinion dated Apr. 13, 2004, for Application No. PCT/US03/12222, International filing date Apr. 21, 2003.

International Preliminary Examination Report dated Aug. 3, 2004, for Application No. PCT/US03/12222, International filing date Apr. 21, 2003.

International Search Report dated Feb. 9, 2004, for Application No. PCT/US03/28329, International filing date Sep. 9, 2003.

Written Opinion dated Jul. 6, 2004, for Application No. PCT/US03/28329, International filing date Sep. 9, 2003.

International Preliminary Examination Report dated Oct. 27, 2004, for Application No. PCT/US03/28329, International filing date Sep. 9, 2003.

International Search Report and Written Opinion dated Jul. 7, 2004, for Application No. PCT/US2004/003922, International filing date Feb. 10, 2004.

International Search Report and Written Opinion dated Jul. 7, 2004, Application No. PCT/US2004/003923, International filing date Feb. 10, 2004.

International Search Report and Written Opinion dated Dec. 8, 2004, for Application No. PCT/US2004/021150, International filing date Jun. 30, 2004.

International Search Report and Written Opinion dated Dec. 30, 2004, for Application No. PCT/US2004/018227, International filing date Jun. 4, 2004.

International Search Report and Written Opinion dated Feb. 1, 2005, for Application No. PCT/US2004/025884, International filing date Aug. 11, 2004.

Invitation to Pay Additional Fees with Partial International Search Report dated May 3, 2005, for Application No. PCT/US2004/037433, International filing date Nov. 10, 2004.

International Search Report and Written Opinion dated Jun. 23, 2005, for Application No. PCT/US2004/037433, International filing date Nov. 10, 2004.

Office Action dated Apr. 3, 2006, for U.S. Appl. No. 10/776,002, filed Feb. 10, 2004.

Notice of Allowance dated Aug. 11, 2006, for U.S. Appl. No. 10/776,002, filed Feb. 10, 2004.

CERTAIN 6, 8-(HETEROARYL OR ARYL) DISUBSTITUTED IMIDAZO[1,2-A]PYRAZINES AS MODULATORS OF HSP90 COMPLEX ACTIVITY

CROSS REFERENCES TO RELATED APPLICATIONS

This application claims priority to U.S. provisional application Ser. No. 60/446,379, filed Feb. 10, 2003, which is hereby incorporated by reference in its entirety.

FIELD OF THE INVENTION

This invention relates to certain imidazo[1,2-a]pyrazin-8-ylamines and related compounds, which when appropriately substituted are modulators of Hsp90 complex activity. Certain compounds provided herein are highly active inhibitors of Hsp90 complex activity. This invention also provides pharmaceutical compositions comprising such compounds, as well as methods for treating a variety of diseases and disorders responsive to Hsp90 complex modulation. Additionally, this invention provides labeled imidazo[1,2-a]pyrazin-8-ylamines as probes for the detection and localization of Hsp90 complex in biological samples.

BACKGROUND

One of the central post-translational control elements in eukaryotic signal transduction is the phosphorylation of the hydroxyl moiety of a kinase serine, threonine, or tyrosine. The phosphorylation state of a given protein can govern its enzyme activity, stability, protein-protein binding interactions, and cellular distribution. Phosphorylation and dephosphorylation is thus a "chemical switch" that allows the cell to transmit signals from the plasma membrane to the nucleus, and to ultimately control gene expression. Kinases are involved in the control of cell metabolism, growth, differentiation, and apoptosis. Kinase signaling mechanisms have been implicated in the onset of cancer, metabolic disorders (for example diabetes), inflammation, immune system disorders, and neurodegeneration. Certain kinases have been implicated in cell proliferation and carcinogenesis. For example, many human cancers are caused by disregulation of a normal protein (e.g., when a kinase proto-oncogene is converted to a kinase oncogene through a gene translocation).

Because kinases are key regulators they are ideal drug design targets. Inhibitors of kinases are among the most important classes of pharmaceutical compounds known. Highly selective, cell-permeable modulators of one or more individual kinases are useful for the treatment of various kinase-implicated disorders. Kinase modulating compounds are additionally useful for the systematic investigation of the cellular function of one or more kinases, and thus, provide valuable tools for the identification of various kinases of therapeutic interest.

Some kinase inhibitors, including tyrosine kinase inhibitors, inhibit T-cell proliferation, and are thus useful as immunosuppressive agents for the prevention or treatment of graft rejection following transplant surgery and for the prevention or treatment of autoimmune diseases such as rheumatoid arthritis and psoriasis.

Kinases also play a critical role in angiogenesis. Angiogenesis, the formation of new blood vessels from preexisting ones, plays a critical role in many pathological settings, including cancer, chronic inflammation, diabetic retinopathy and macular degeneration. Angiogenesis is regulated by multiple cell-signaling pathways, including pathways controlled by cellular kinases. Blocking angiogenesis, through the modulation of cell kinases, therefore, represents an effective approach to the treatment of diseases such as cancer.

The process of angiogenesis is complex, requiring the concerted actions of multiple angiogenic mediators as well as the participation of different cell types. Key angiogenesis mediators, including vascular endothelial growth factor (VEGF), fibroblast growth factor (FGF), and angiopoietin 1 and 2 (Ang1 and Ang2) that bind to their cognate receptors (VEGFRs, FGFRs and Tie1 and Tie2, respectively) expressed on endothelial cells, as well as platelet-derived growth factor (PDGF) that binds to its receptor (PDGFRs) expressed on pericytes and smooth muscle cells, have been identified. Recent studies indicate that several members of the ephrin family and their receptor Eph family are novel regulators of vascular differentiation and development that have also been implicated in the angiogenesis in tumors. Thus, inhibitors of EphB4 tyrosine kinase are desirable as anti-cancer agents and anti-angiogenesis agents.

Concurrent modulation of multiple cell-signaling pathways is also desirable for the treatment of cancer. Oncogenic signaling pathways have been shown to be mediated by kinase activity; therefore, modulating these oncogenic kinases is desirable for the treatment of cancer. Kinases that have been implicated in oncogenic signaling include, but are not limited to: EGFR, ErB2, c-Kit, PDGFRα, and Flt3.

Many of the cellular processes regulated by kinases are further regulated by Hsp90.

Hsp90 is a molecular chaperone, a class of proteins that regulates protein folding in cells. Hsp90 is a 90 kD protein that functions as a homodimer. Hsp90 regulates its own expression by sequestering the transcription factor, HSF1, under non-stress conditions. Upon heat shock, HSF1 is released from Hsp90 leading to transcription and increased synthesis of Hsp90, thereby controlling the cellular stress response.

Numerous contacts in the 190 C-terminal amino acids of the protein are responsible for dimerization of this protein. The 25 kD $NH_2$-terminal of Hsp90 contains an ATP binding site, where ATP is bound and subsequently hydrolyzed. Thus Hsp90 is an ATPase, and has been classified as a member of the GHKL ATPase superfamily. It is believed that unfolded, or partially folded substrate proteins, also called Hsp90 client proteins, are stably bound to Hsp90 in its ATP bound state, and released upon ATP hydrolysis.

Hsp90 is an important cell cycle regulatory protein, implicated in the correct folding of multiple proteins in the mitogenic signal cascade. Hsp90 also plays a role in cyclin dependent progression through G1 and G2 and in centrosome function in mitosis. Hsp90 substrates include a number of steroid hormone receptors including the androgen receptor (AR), estrogen receptor, and glucocorticoid receptor.

Hsp90 has been specifically implicated in the proper folding of a number of tyrosine and threonine kinases. It also insures the correct folding and activity of numerous kinases involved in cell proliferation and differentiation, many of which also play roles in oncogenesis.

Hsp90 can also function as part of a multi-component complex interacting with many other co-chaperone proteins. While Hsp90 forms a multi-component complex to some extent in normal cells, nearly all Hsp90 present in cultured tumor cells has been shown to be part of a multi-component complex. A number of known oncogenic proteins that are Hsp90 substrate proteins, depend on the chaperone activity of the Hsp90 complex for correct folding. Thus Hsp90 functions as a supplier of oncogenic proteins in tumor cells. Hsp90 complex in tumor cells also exhibits higher ATPase activity than Hsp90 from non-cancerous cell lines.

Geldanamycin, a natural product, is an Hsp 90 inhibitor that binds to the ATP binding site of Hsp90 inhibiting ATP hydrolysis but not substrate protein binding. Substrate proteins that reside longer on Hsp90 when ATP hydrolysis is inhibited are ubiquinated, and subsequently degraded. Disrupting the function of the Hsp90 complex has been shown to deplete oncogenic kinases (via ubiquitin-mediated proteasomal degradation) and decrease tumor growth. The Hsp90 complex present in tumor cells exhibits much higher affinity for geldanamycin and for 17-AAG, a geldanamycin derivative, than Hsp90 in non-tumor cells. Thus inhibitors of the Hsp90 complex have the ability to convert this protein from a chaperone that insures correct protein folding of oncogenic proteins to a selective protein degradation tool.

Because of its roles in cell cycle control, cell growth, and oncogenesis the Hsp90 complex is an important target for anti-cancer therapeutics. The ability of certain Hsp90 complex inhibitors to cause this protein complex to selectively target its substrate proteins for degradation makes the Hsp90 complex an especially desirable anti-cancer target. Hsp90 is also a potential drug target for autoimmune and degenerative disease because of its role in modulating the cellular stress response.

Agents capable of modulating the Hsp90 complex, are highly desirable for the treatment of a variety of diseases and disorders, including cancer. Small molecule, non-peptide antagonists of the Hsp90 complex are of particular value for such therapies. The present invention fulfills this need, and provides further related advantages.

SUMMARY OF THE INVENTION

The invention provides modulators of kinase activity and Hsp90 complex activity which may generally be described as substituted imidazo[1,2-a]pyrazin-8-ylamines and related compounds. Certain compounds provided herein are highly active inhibitors of Hsp90 complex activity.

Thus, the invention includes compounds of Formula I:

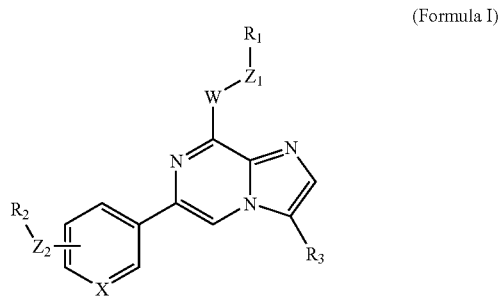

(Formula I)

and the pharmaceutically acceptable forms thereof.

In Formula I the variables $R_1$, $R_2$, $R_3$, $Z_1$, $Z_2$, W, and X are defined as follows:

$R_1$ is hydrogen, halogen, $C_1$–$C_7$alkyl, $C_1$–$C_6$alkoxy, ($C_3$–$C_7$cycloalkyl)$C_0$–$C_2$alkyl, (heterocycloalkyl) $C_0$–$C_2$alkyl, sulfonamide, ($C_1$–$C_6$alkoxy)$C_1$–$C_6$alkyl, ($C_1$–$C_6$alkoxy)$C_1$–$C_6$alkoxy, mono- or di-($C_1$–$C_6$alkyl) amino, or mono- or di-($C_1$–$C_6$alkyl)amino ($C_1$–$C_6$alkyl); or $R_1$ is phenyl, phenyl fused to a 5 to 7-membered heterocycloalkyl ring containing 1 or 2 heteroatoms chosen from N, O, and S, or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, $C_1$–$C_6$alkylthio, ($C_1$–$C_6$alkoxy)$C_1$–$C_6$alkyl, ($C_1$–$C_6$alkoxy) $C_1$–$C_6$alkoxy, mono- and di-($C_1$–$C_6$alkyl)amino, amino($C_1$–$C_6$alkyl), mono- and di-($C_1$–$C_6$alkyl)amino ($C_1$–$C_6$alkyl), $C_2$–$C_6$alkanoyl, and —C(O)$R_{13}$ where $R_{13}$ is $C_1$–$C_3$haloalkyl, phenyl, heterocycloalkyl, or heteroaryl.

$Z_1$ is

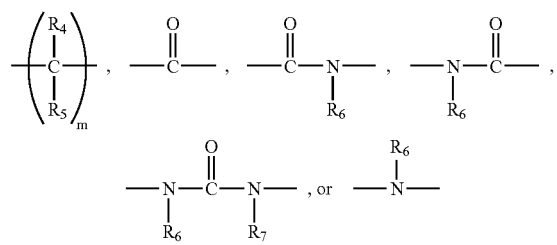

wherein $R_4$ and $R_5$ are independently hydrogen, $C_1$–$C_6$alkyl, sulfonamide, or halogen; and m is 0, 1, or 2; $R_6$ and $R_7$ are independently (i) hydrogen or $C_1$–$C_6$alkyl or ii) phenyl or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino ($C_1$–$C_6$alkyl), mono- and di-($C_1$–$C_6$alkyl)amino ($C_1$–$C_6$alkyl), $C_2$–$C_6$alkanoyl, and —C(O)$R_{13}$.

W is phenyl or a 5- or 6-membered heteroaryl containing from 1 to 4 heteroatoms independently chosen from nitrogen, oxygen, and sulfur; wherein W is substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl.

X is N or CH.

$R_2$ is $C_1$–$C_7$alkyl, $C_3$–$C_7$cycloalkyl($C_0$–$C_2$alkyl), heterocycloalkyl($C_0$–$C_2$alkyl), $C_1$–$C_6$alkoxy, ($C_1$–$C_6$alkoxy) $C_1$–$C_6$alkyl, or ($C_1$–$C_6$alkoxy)$C_1$–$C_6$alkoxy; or $R_2$ is phenyl($C_0$–$C_2$alkyl) or heteroaryl($C_0$–$C_2$alkyl), each of which is substituted with 0 to 3 substituents independently chosen from (i) hydroxy, halogen, nitro, cyano, amino, sulfonamide, —CHO, $C_1$–$C_6$haloalkyl, and $C_1$–$C_6$haloalkoxy, and (ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy)$C_1$–$C_6$alkyl, ($C_1$–$C_6$alkoxy)$C_1$–$C_6$-alkoxy, $C_1$–$C_6$alkylthio, monoand di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, heterocycloalkyl($C_0$–$C_2$alkyl), and —C(O)$R_{13}$; each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl)amino.

$Z_2$ is

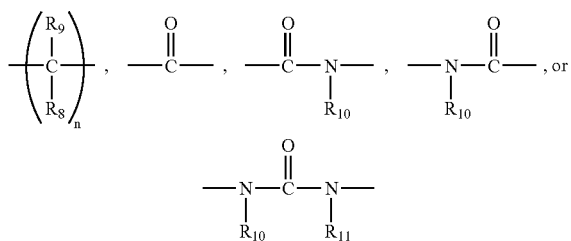

wherein $R_8$ and $R_9$ are independently hydrogen, $C_1$–$C_6$alkyl, $C_1$–$C_6$alkoxy, or halogen; and n is 0, 1, or 2; and $R_{10}$ and $R_{11}$ are independently (v) hydrogen or $C_1$–$C_6$alkyl; or (vi) phenyl or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)$R_{13}$.

$R_3$ is hydrogen or $C_1$–$C_6$alkyl, or $R_3$ is $C_3$–$C_7$cycloalkyl($C_0$–$C_2$alkyl), heterocycloalkyl($C_0$–$C_2$alkyl), phenyl, or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)$R_{13}$; or $R_3$ is phenoxyphenyl, each of which phenyl rings is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)$R_{13}$.

In certain embodiments the invention includes compounds of Formula I, which exhibit an $IC_{50}$ of 5 micromolar or less, 1 micromolar or less, or 500 nanomolar or less in an in vitro assay of tumor cell proliferation, such as the cell proliferation assay described in Example 11.

The invention includes a pharmaceutical composition, comprising one or more compounds Formula I or any pharmaceutically acceptable form thereof, together with at least one pharmaceutically acceptable carrier or excipient.

The invention also pertains to packaged pharmaceutical compositions which comprise a pharmaceutical composition, comprising one or more compounds Formula I or any pharmaceutically acceptable form thereof, together with at least one pharmaceutically acceptable carrier or excipient in a container and with instructions for using the pharmaceutical composition to treat a patient suffering from a disease or disorder responsive to Hsp90 complex modulation.

The invention further pertains to a method for modulating binding of ATP to the Hsp90 complex, the method comprising contacting a cell or cells expressing the Hsp90 complex with a compound according to Formula I or form thereof in an amount sufficient to detectably decrease the level of an Hsp90 substrate protein in vitro. In certain embodiments the Hsp90 substrate protein is Raf, Akt, or ErbB2.

Furthermore the invention includes a method for treating a patient having a disease or disorder responsive to Hsp90 complex modulation, comprising administering to the patient and effective amount of a compound or form thereof according to Formula I. The invention includes methods of treatment in which the patient is a human patient, and in which the patient is a companion animal, such as a cat or dog, and in which the patient is a livestock animal, such as a horse, cow, or pig. The invention particularly includes methods in which the disease or disorder responsive to Hsp90 complex modulation is cancer, an autoimmune disease, inflammation, or a neurodegenerative disease.

Methods of treatment include administering a compound of Formula I as a single active agent or administering a compound of Formula I in combination with one or more other active agent.

The invention includes a method for determining the presence or absence of Hsp90 complex in a sample comprising contacting the sample with a compound or form thereof of Formula I under conditions that permit binding of the compound or form to the Hsp90 complex, detecting a level of the compound or form bound to the Hsp90 complex, and therefrom determining the presence or absence of Hsp90 complex.

DETAILED DESCRIPTION OF THE INVENTION

Certain terms to be used herein are provided prior to setting forth the invention in detail. Compounds of the present invention are described using standard nomenclature. Unless defined otherwise, all technical and scientific terms used herein have the same meaning as is commonly understood by one of skill in the art to which this invention belongs.

Chemical Description and Terminology

Formula I includes all subformulae thereof. For example Formula I includes compounds of Formulas 1 to 14.

Certain compounds are described herein using a general formula that includes variables, e.g. $R_1$, $R_2$, $R_3$, W, X, $Z_1$, and $Z_2$. Unless otherwise specified, each variable within such a formula is defined independently of other variables.

In accordance with the usual meaning of "a" and "the" in patents, reference to "a" kinase or "the" kinase is inclusive of one or more kinases. Unless otherwise specified the term "compounds" includes all pharmaceutically acceptable forms of the disclosed structures.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral KPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on a "substituted" position include, but are not limited to, e.g., halogen; cyano; hydroxyl; nitro; azido; alkanoyl (such as a $C_2$–$C_6$ alkanoyl group such as acyl or the like); carboxamido; alkyl groups (typically having 1 to about 8 carbon atoms, or 1 to about 6 carbon atoms); cycloalkyl groups, alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O, or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen or amino.

A dash ("-") that is not between two letters or symbols is used to indicate a point of attachment for a substituent. For example, —CHO is attached through carbon of the carbonyl (C=O) group.

As used herein, "alkyl" includes both branched and straight chain saturated aliphatic hydrocarbon groups, having the specified number of carbon atoms, generally from 1 to about 12 carbon atoms. The term $C_1$–$C_7$alkyl as used herein indicates an alkyl group having from 1 to about 7 carbon atoms. When $C_0$–$C_n$alkyl is used herein in conjunction with another group, for example, heterocycloalkyl ($C_0$–$C_2$alkyl), the indicated group, in this case heterocycloalkyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, 3-methylbutyl, t-butyl, n-pentyl, and sec-pentyl. Alkyl groups described herein typically have from 1 to about 12 carbons atoms. Preferred alkyl groups are lower alkyl groups, those alkyl groups having from 1 to about 8 carbon atoms, from 1 to about 6 carbon atoms, or from 1 to about 4 carbons atoms e.g. $C_1$–$C_8$, $C_1$–$C_6$, and $C_1$–$C_4$alkyl groups.

"Alkenyl" as used herein, indicates a straight or branched hydrocarbon chain comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. $C_2$–$C_8$, $C_2$–$C_6$, and $C_2$–$C_4$ alkenyl groups. Examples of alkenyl groups include ethenyl, propenyl, and butenyl groups.

"Alkynyl" as used herein, indicates a straight or branched hydrocarbon chain comprising one or more triple carbon-carbon bonds that may occur in any stable point along the chain, such as ethynyl and propynyl. Alkynyl groups described herein typically have from 2 to about 12 carbons atoms. Preferred alkynyl groups are lower alkynyl groups, those alkynyl groups having from 2 to about 8 carbon atoms, e.g. $C_2$–$C_8$, $C_2$–$C_6$, and $C_2$–$C_4$ alkynyl groups "Alkoxy" indicates an alkyl group as defined above with the indicated number of carbon atoms attached through an oxygen bridge (—O—). Examples of alkoxy include, but are not limited to, methoxy, ethoxy, n- propoxy, i- propoxy, n-butoxy, 2-butoxy, t-butoxy, n-pentoxy, 2-pentoxy, 3- pentoxy, isopentoxy, neopentoxy, n-hexoxy, 2-hexoxy, 3-hexoxy, and 3-methylpentoxy.

In the term "(Alkoxy)alkyl" alkoxy and alkyl are as defined above and the point of attachment is on the alkyl group. For example ($C_1$–$C_6$alkoxy)$C_1$–$C_6$alkyl indicates an alkoxy group have from 1 to about 6 carbon atom attached through its oxygen atom to an alkyl group have from 1 to about 6 carbon atoms and further attached to the core molecule through a carbon atom in the $C_1$–$C_6$alkyl portion.

In the term "(Alkoxy)alkoxy" alkoxy is as defined above and the point of attachment is on the oxygen of the second listed alkoxy group. For example ($C_1$–$C_6$alkoxy)

$C_1$–$C_4$alkoxy indicates an alkoxy group have from 1 to about 6 carbon atom attached through its oxygen atom to an second alkoxy group, this one having from 1 to about 4 carbon atoms and further attached to the core molecule through an oxygen bridge.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, "alkylthio" means alkyl-S—, where the alkyl group is an alkyl group as defined above having the defined number of carbon atoms. An exemplary alkylthio group is methylthio.

As used herein the term "alkoxycarbonyl" indicates an alkoxy group, as defined above, having the indicated number of carbon atoms, attached through a keto (—(C=O)—) bridge. The alkoxy moiety of the alkoxycarbonyl group has the indicated number of carbon atoms. The carbon of the keto bridge is not included in this number. $C_3$alkoxycarbonyl indicates for example, groups of the formula $CH_3(CH_2)_2$—O—(C=O)— or $(CH_3)_2(CH)$—O—(C=O)—.

As used herein "amino(alkyl)" is an alkyl group as defined herein, having the indicated number of carbon atoms, and substituted with at least one amino substituent (—$NH_2$). When indicated aminoalkyl groups, like other groups described herein, may be additionally substituted.

As used herein, the term "mono- and/ or di-(alkyl)amino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and/or di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

As used herein, the term "mono- and/or di-(alkyl)amino (alkyl)" indicates a mono- and/or di-(alkyl) group as defined attached through an alkyl linker having the specified number of carbon atoms.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

"Cycloalkyl" as used herein, indicates a monocyclic or multicyclic saturated hydrocarbon ring group, having the specified number of carbon atoms, usually from 3 to about 10 ring carbon atoms. Monocyclic cycloalkyl groups typically have from 3 to about 8 carbon ring atoms or from 3 to about 7 carbon ring atoms. Multicyclic cycloalkyl groups may have 2 or 3 fused cycloalkyl rings or contain bridged or caged cycloalkyl groups. Cycloalkyl substituents may be pendant to the substituted nitrogen or carbon atom, or where a substituted carbon atom may have two substituents a cycloalkyl group may be attached as a spiro group. Examples of cycloalkyl groups include cyclopropyl, cyclobutyl, cyclopentyl, or cyclohexyl as well as bridged or caged saturated ring groups such as norbornane or adamantane.

As used herein "Cycloalkyl($C_0$–$C_2$alkyl) indicates a cycloalkyl groups as defined above either directly attached via a single covalent bond or attached through an ethylene (—$CH_2CH_2$—) or methylene (—$CH_2$—) linker.

As used herein "haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic aromatic ring which contains from 1 to 4, or preferably from 1 to 2, heteroatoms chosen from N, O, and S, with remaining ring atoms being carbon, or a stable bicyclic or tricyclic system containing at least one 5 to 7 membered aromatic ring which contains from 1 to 4, or preferably from 1 to 2, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d] oxazolyl, benzofuranyl, benzothiazolyl, benzothiophenyl, benzoxadiazolyl, dihydrobenzodioxynyl, furanyl, imidazolyl, indolyl, and isoxazolyl.

The term "heterocycloalkyl" indicates a saturated monocyclic group containing from 1 to about 3 heteroatoms chosen from N, O, and S, with remaining ring atoms being carbon, or a saturated bicyclic ring system having at least one N, O, or S ring atom with remaining atoms being carbon. Monocyclic heterocycloalkyl groups have from 4 to about 8 ring atoms, and more typically have from 5 to 7 ring atoms. Bicyclic heterocycloalkyl groups typically have from about five to about 12 ring atoms. The number of ring atoms size of a heterocycloalkyl groups is given by the number of ring carbon atoms the group contains. For example, a $C_2$–$C_7$heterocycloalkyl group contains from 2 to about 7 ring carbon atoms with the remaining ring atoms, up to about 3 per ring, being chosen from N, O, and S. Preferred heterocycloalkyl groups include $C_3$–$C_6$ monocyclic heterocycloalkyl groups that contain from 5 to 7 ring atoms and 1 or 2 heteroatoms independently chosen from N, O, and S. Examples of heterocycloalkyl groups include morpholinyl, piperazinyl, piperidinyl, and pyrrolidinyl groups.

In the term "heterocycloalkyl(alkyl)" the groups heterocycloalkyl and alkyl are as defined above and the point of attachment to the core structure is on the alkyl group.

By "sulfonamide" is meant —S(O)$_2$N— in either S-linked or N-linked orientation, where the nitrogen atom can be unsubstituted or mono- or di-substituted, for example with $C_3$–$C_6$cycloalkylmethyl, straight or branched chain $C_1$–$C_7$alkyl.

"Pharmaceutically acceptable forms" of the compounds recited herein include pharmaceutically acceptable salts, hydrates, solvates, crystal forms, polymorphs, chelates, non-covalent complexes, esters, clathrates, prodrugs, and mixtures of such compounds.

"Pharmaceutically acceptable salts" include derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0–4, and the like. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "active agent" is used to indicate a compound, including any pharmaceutically form thereof, or natural product, which has biological activity. Preferably an "active agent" is a compound having pharmaceutical utility. For example an active agent may be an anti-cancer therapeutic.

The term "effective amount" or an of a compound of this invention means an amount effective, when administered to a human or non-human patient, to provide a therapeutic benefit such as an amelioration of symptoms, e.g., an amount effective to decrease the symptoms of a disease or disorder responsive to kinase or Hsp90 complex modulation, and preferably an amount sufficient to reduce cancer symptoms, decrease the number of detectable cancerous cells in an organism, detectably slow or stop the growth of a cancerous tumor, or more preferably and amount sufficient to shrink a cancerous tumor. In certain circumstances a patient suffering from cancer may not present symptoms of being infected. Thus a therapeutically effective amount of a compound is also an amount sufficient to prevent a significant increase or significantly reduce the detectable level of cancerous cells or cancer markers in the patient's blood, serum, or tissues. A significant increase or reduction in the detectable level of cancerous cells or cancer markers is any detectable change that is statistically significant in a standard parametric test of statistical significance such as Student's T-test, where $p<0.05$.

Imidazo[1,2-a]Pyrazine Compounds

In addition to compounds of Formula I described above, the invention also includes compounds of Formula 1

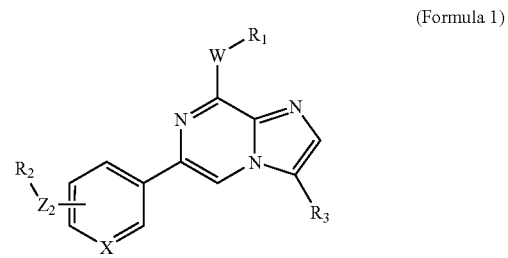

(Formula 1)

and the pharmaceutically forms thereof, wherein:

$R_1$ is hydrogen, halogen, $C_1$–$C_7$alkyl, $C_1$–$C_6$alkoxy, $C_3$–$C_7$cycloalkyl($C_0$–$C_2$alkyl), heterocycloalkyl ($C_0$–$C_2$alkyl), sulfonamide, ($C_1$–$C_6$alkoxy)$C_1$–$C_6$alkyl, ($C_1$–$C_6$alkoxy)$C_1$–$C_6$alkoxy, mono- or di-($C_1$–$C_6$alkyl) amino, or mono- or di-($C_1$–$C_6$alkyl)amino ($C_1$–$C_6$alkyl); or $R_1$ is phenyl or phenyl fused to a 5 to 7-membered heterocycloalkyl ring containing 1 or 2 heteroatoms chosen from N, O, and S, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, $C_1$–$C_6$alkylthio, ($C_1$–$C_6$alkoxy)$C_1$–$C_6$alkyl, ($C_1$–$C_6$alkoxy) $C_1$–$C_6$alkoxy, mono- and di-($C_1$–$C_6$alkyl)amino, amino($C_1$–$C_6$alkyl), mono- and di-($C_1$–$C_6$alkyl)amino ($C_1$–$C_6$alkyl), $C_2$–$C_6$alkanoyl, and —C(O)$R_{13}$ where $R_{13}$ is $C_1$–$C_3$haloalkyl, phenyl, heterocycloalkyl, or heteroaryl.

W is phenyl or a 5- or 6-membered heteroaryl containing from 1 to 4 heteroatoms independently chosen from nitrogen, oxygen, and sulfur; wherein W is substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl.

X is N or CH.

$R_2$ is $C_1$–$C_7$alkyl, $C_3$–$C_7$cycloalkyl($C_0$–$C_2$alkyl), heterocycloalkyl($C_0$–$C_2$alkyl), $C_1$–$C_6$alkoxy, ($C_1$–$C_6$alkoxy) $C_1$–$C_6$alkyl, or ($C_1$–$C_6$alkoxy)$C_1$–$C_6$alkoxy; or $R_2$ is phenyl(C₀–C₂alkyl) or heteroaryl(C₀–C₂alkyl), each of which is substituted with 0 to 3 substituents independently chosen from (i) hydroxy, halogen, nitro, cyano, amino, sulfonamide, —CHO, $C_1$–$C_6$haloalkyl, and $C_1$–$C_6$haloalkoxy, and (ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, heterocycloalkyl(C₀–C₂alkyl), and —C(O)R₁₃; each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl)amino;

$Z_2$ is

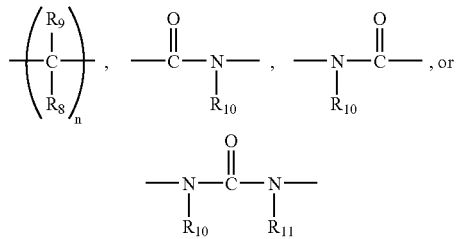

wherein R₈ and R₉ are independently hydrogen, $C_1$–$C_6$alkyl, $C_1$–$C_6$alkoxy, or halogen; and n is 0, 1, or 2; R₁₀ and R₁₁ are independently (iii) hydrogen or $C_1$–$C_6$alkyl; or (iv) phenyl or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)R₁₃.

R₃ is hydrogen or $C_1$–$C_6$alkyl, or R₃ is $C_3$–$C_7$cycloalkyl(C₀–C₂alkyl), heterocycloalkyl(C₀–C₂alkyl), phenyl, or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$ alkyl), mono- and di-($C_1$–$C_6$alkyl)amino($C_1$–$C_6$alkyl), $C_2$–$C_6$alkanoyl, and —C(O)R₁₃; or R₃ is phenoxy phenyl, each of which phenyl rings is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)R₁₃

The invention further includes compounds of the same Formula 1 in which the variables R₁, R₂, R₃, Z₂, W, and X are defined as follows:

R₁ is hydrogen, halogen, $C_1$–$C_7$alkyl, $C_1$–$C_6$alkoxy, $C_3$–$C_7$cycloalkyl(C₀–C₂alkyl), heterocycloalkyl(C₀–C₂alkyl), sulfonamide, ($C_1$–$C_6$alkoxy)$C_1$–$C_6$alkyl, ($C_1$–$C_6$alkoxy)$C_1$–$C_6$alkoxy, mono- or di-($C_1$–$C_6$alkyl) amino, or mono- or di-($C_1$–$C_6$alkyl)amino ($C_1$–$C_6$alkyl); or R₁ is phenyl or a 5- or 6-membered heteroaryl ring containing 1 or 2 heteroatoms, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl.

W is phenyl or a 5- or 6-membered heteroaryl ring; substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl.

X is N or CH.

R₂ is $C_1$–$C_7$alkyl, $C_3$–$C_7$cycloalkyl(C₀–C₂alkyl), heterocycloalkyl, (heterocycloalkyl)$C_1$–$C_2$alkyl, $C_1$–$C_6$alkoxy, ($C_1$–$C_6$alkoxy)$C_1$–$C_6$alkyl, or ($C_1$–$C_6$alkoxy)$C_1$–$C_6$alkoxy; or R₂ is phenyl(C₀–C₂alkyl) or 5- or 6-membered heteroaryl (C₀–C₂alkyl), each of which is substituted with 0 to 3 substituents independently chosen from (i) hydroxy, halogen, nitro, cyano, amino, sulfonamide, —CHO, $C_1$–$C_6$haloalkyl, and $C_1$–$C_6$haloalkoxy, and (ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), $C_2$–$C_6$alkanoyl, and heterocycloalkyl (C₀–C₂alkyl); each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl) amino.

$Z_2$ is

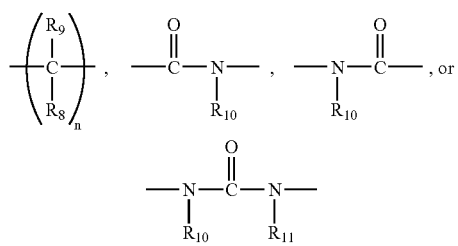

wherein R₈ and R₉ are independently hydrogen, $C_1$–$C_6$alkyl, $C_1$–$C_6$alkoxy, or halogen; R₁₀ and R₁₁ are independently (iii) hydrogen or $C_1$–$C_6$alkyl; or (iv) phenyl or a 5- or 6 membered heteroaryl ring, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

$R_3$ is hydrogen or $C_1$–$C_6$alkyl, or $R_3$ is $C_3$–$C_7$cycloalkyl($C_0$–$C_2$alkyl), heterocycloalkyl($C_0$–$C_2$alkyl), phenyl, or a 5- or 6-membered heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl; or $R_3$ is phenoxyphenyl, each of which phenyl rings is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

Such compounds will be referred to as compounds of Formula 1-A.

The $R_1$ Variable

The invention includes compounds and pharmaceutically acceptable forms of Formula 1 and 1-A in which:

$R_1$ is halogen, $C_1$–$C_7$alkyl, $C_1$–$C_6$alkoxy, ($C_3$–$C_7$cycloalkyl)$C_0$–$C_2$alkyl, or (heterocycloalkyl)$C_0$–$C_2$alkyl; or $R_1$ is phenyl substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

In other embodiments the invention includes compounds and pharmaceutically acceptable forms of Formula 1 and Formula 1-A in which:

$R_1$ is halogen or $C_1$–$C_7$alkyl; or $R_1$ is phenyl substituted with 0 to 3 substituents independently chosen from hydroxy, nitro, cyano, amino, halogen, $C_1$–$C_6$alkyl, $C_3$–$C_7$cycloalkyl, $C_1$–$C_6$alkoxy, $C_1$–$C_2$haloalkyl, $C_1$–$C_2$haloalkoxy, and mono- and di-($C_1$–$C_4$alkyl)amino.

Also included in the invention are compounds and pharmaceutically acceptable forms of Formula 1 and Formula 1-A in which:

$R_1$ is phenyl substituted with 0 to 3 substituents independently chosen from hydroxy, nitro, cyano, amino, halogen, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl)amino.

The invention also pertains to compounds and pharmaceutically acceptable forms of Formula 1 and Formula 1-A in which: $R_1$ is bromo or $C_1$–$C_4$alkyl; or $R_1$ is phenyl substituted with 0 to 2 substituents independently chosen from fluoro, chloro, bromo, $C_1$–$C_2$alkyl, and $C_1$–$C_2$alkoxy.

The W Variable

The invention includes compounds and pharmaceutically acceptable forms of Formula 1 and Formula 1-A in which:

W is phenyl, pyridyl, pyrimidinyl, imidazolyl, pyrrolyl, pyrazolyl, furanyl, thienyl, oxazolyl, or isoxazolyl, each of which is substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

The invention also includes compounds and pharmaceutically acceptable forms of Formula 1 and Formula 1-A in which:

W is phenyl, pyridyl, pyrimidinyl, imidazolyl, pyrrolyl, pyrazolyl, furanyl, thienyl, oxazolyl, or isoxazolyl, each of which is substituted with 0 to 3 substituents independently chosen from hydroxy, nitro, cyano, amino, halogen, oxo, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl)amino.

Other embodiments of the invention include compounds and pharmaceutically acceptable forms of Formula 1 and 1-A in which:

W is imidazolyl, pyrrolyl, or pyrazolyl, each of which is substituted with 0 to 3 substituents independently chosen from hydroxy, cyano, halogen, oxo, $C_1$–$C_4$alkyl, $C_1$–$C_4$alkoxy, trifluoromethyl, and trifluoromethoxy.

The invention includes compounds and pharmaceutically acceptable forms in which W is an imidazolyl group substituted with $R_1$ at the 4-position or at the 2-position, i.e. compounds of Formula 2 and Formula 3:

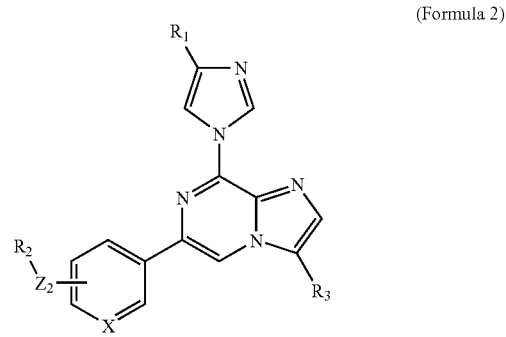

(Formula 2)

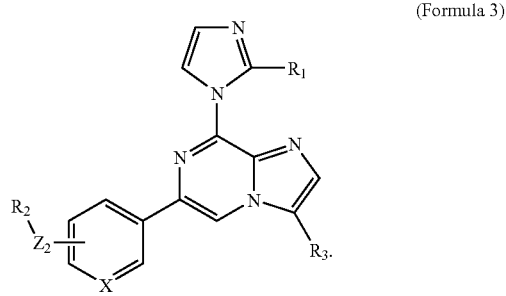

(Formula 3)

The invention includes compounds and pharmaceutically acceptable forms in which W is a pyrazolyl group substituted with $R_1$ at the 3-position, i.e., compounds of Formula 4:

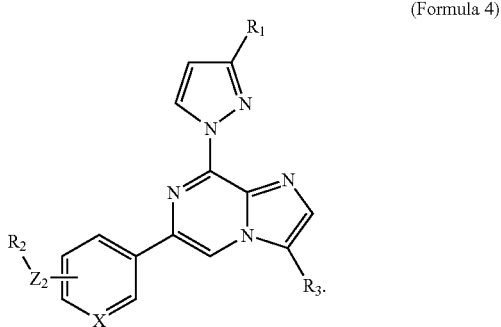

(Formula 4)

The X Variable:

The invention includes compounds and pharmaceutically acceptable forms of Formula 1 and Formula 1-A in which X is N. In other embodiments X is CH.

The $Z_2$ Variable

The invention includes compounds and pharmaceutically acceptable forms of Formula 1 and Formula 1-A in which: $Z_2$ is

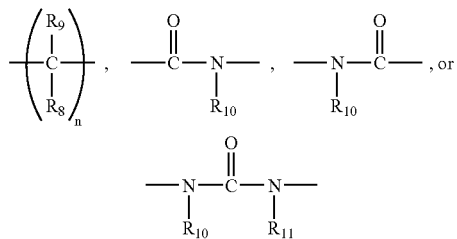

wherein $R_8$ and $R_9$ are independently hydrogen or $C_1$–$C_6$alkyl; n is 0, 1, or 2; and $R_{10}$ and $R_{11}$ are independently hydrogen, $C_1$–$C_6$alkyl, or phenyl.

The invention includes compounds and pharmaceutically acceptable forms of Formula 1 and Formula 1-A in which: $Z_2$ is

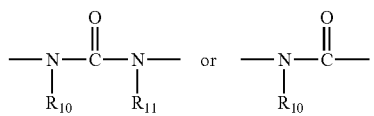

wherein, $R_{10}$ and $R_{11}$ are independently hydrogen, methyl or ethyl.

In certain embodiments $R_{10}$ and $R_{11}$ are both hydrogen.

The $R_2$ Variable

The invention includes compounds and pharmaceutically acceptable forms of Formula 1 and Formula 1-A in which:

$R_2$ is phenyl, pyridyl, pyrimidinyl, pyrazinyl, imidazolyl, pyrrolyl, furanyl, thienyl, oxazolyl, or isoxazolyl, each of which may be either directly attached or bound via a $C_1$–$C_2$alkyl linker, and each of which is substituted with 0 to 3 substituents independently chosen from: (i) hydroxy, halogen, nitro, cyano, amino, sulfonamide, —CHO, $C_1$–$C_6$haloalkyl, and $C_1$–$C_6$haloalkoxy, and (ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), $C_2$–$C_6$alkanoyl, and heterocycloalkyl ($C_0$–$C_2$alkyl); each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl) amino.

In other embodiments the invention includes compounds and pharmaceutically acceptable forms of Formula 1 and Formula 1-A in which:

$R_2$ is phenyl($C_0$–$C_2$alkyl), pyridyl($C_0$–$C_2$alkyl), or pyrimidinyl($C_0$–$C_2$alkyl), each of which is substituted with 0 to 3 substituents independently chosen from: (i) hydroxy, halogen, nitro, cyano, amino, $C_1$–$C_2$haloalkyl, and $C_1$–$C_2$haloalkoxy, and (ii) $C_1$–$C_6$alkyl, $C_3$–$C_7$cycloalkyl, $C_1$–$C_6$alkoxy, ($C_1$–$C_6$alkoxy)$C_1$–$C_6$alkyl, mono- and di-($C_1$–$C_4$alkyl) amino, mono- and di-($C_1$–$C_4$alkyl)amino($C_1$–$C_4$alkyl), and heterocycloalkyl($C_0$–$C_2$alkyl); each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl)amino.

The invention further includes compounds and pharmaceutically acceptable forms of Formula 1 and Formula 1-A in which:

$R_2$ is phenyl, pyridyl, or pyrimidinyl, each of which is substituted with 0 to 3 substituents independently chosen from hydroxy, nitro, cyano, amino, halogen, $C_1$–$C_6$alkyl, $C_3$–$C_7$cycloalkyl, $C_1$–$C_6$alkoxy, $C_1$–$C_2$haloalkyl, $C_1$–$C_2$haloalkoxy, and mono- and di-($C_1$–$C_4$alkyl)amino.

The $R_3$ Variable

The invention includes compounds and pharmaceutically acceptable forms of Formula I and Formula 1-A in which:

$R_3$ is hydrogen or $C_1$–$C_6$alkyl, or $R_3$ is $C_3$–$C_7$cycloalkyl ($C_0$–$C_2$alkyl), heterocycloalkyl($C_0$–$C_2$alkyl), phenyl, phenyl, pyridyl, pyrimidinyl, pyrazinyl, imidazolyl, pyrrolyl, furanyl, thienyl, oxazolyl, or isoxazolyl, each of which is substituted with 0 to 3 substituents independently chosen from hydroxy, nitro, cyano, amino, halogen, $C_1$–$C_6$alkyl, $C_3$–$C_7$cycloalkyl, $C_1$–$C_6$alkoxy, $C_1$–$C_2$haloalkyl, $C_1$–$C_2$haloalkoxy, and mono- and di-($C_1$–$C_4$alkyl)amino; or $R_3$ is phenoxy phenyl, each of which phenyl rings is substituted with 0 to 3 substituents independently chosen from hydroxy, nitro, cyano, amino, halogen, $C_1$–$C_6$alkyl, $C_3$–$C_7$cycloalkyl, $C_1$–$C_6$alkoxy, $C_1$–$C_2$haloalkyl, $C_1$–$C_2$haloalkoxy, and mono- and di-($C_1$–$C_4$alkyl)amino.

Further included are compounds and pharmaceutically acceptable forms of Formula I and Formula 1-A in which:

$R_3$ is hydrogen, $C_1$–$C_6$alkyl, $C_3$–$C_7$cycloalkyl ($C_0$–$C_2$alkyl), phenyl, or phenoxyphenyl. In some preferred embodiments $R_3$ is hydrogen or $C_1$–$C_4$alkyl.

Formulas 6, 7, and 8

The invention pertains to compounds and pharmaceutically acceptable forms of Formula 6

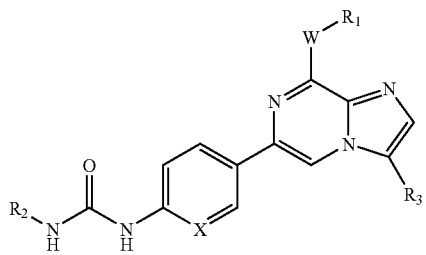
(Formula 6)

in which $R_1$, $R_2$, $R_3$, X, W, and $Z_1$ may carry any of the definitions set forth above for these variables.

The invention further pertains to compounds and pharmaceutically acceptable forms of Formula 7

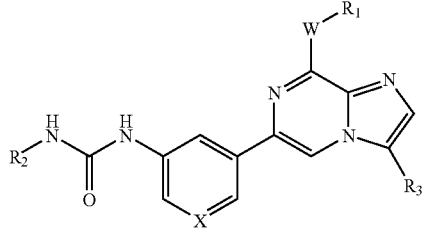
(Formula 7)

in which $R_1$, $R_2$, $R_3$, X, W, and $Z_1$ may carry any of the definitions set forth above for these variables.

The invention pertains to compounds and pharmaceutically acceptable forms of Formula 8

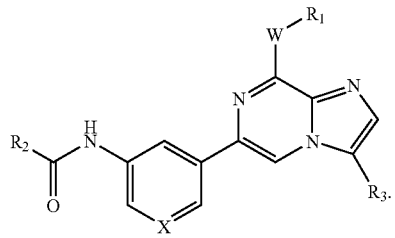
(Formula 8)

in which $R_1$, $R_2$, $R_3$, X, W, and $Z_1$ may carry any of the definitions set forth above for these variables.

The invention pertains to compounds and pharmaceutically acceptable forms of Formula 9 to 14:

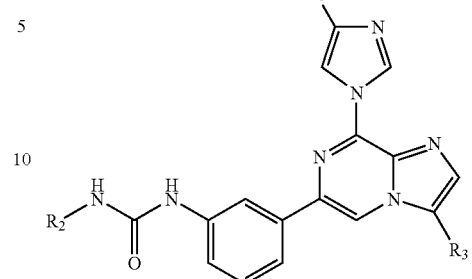
(Formula 9)

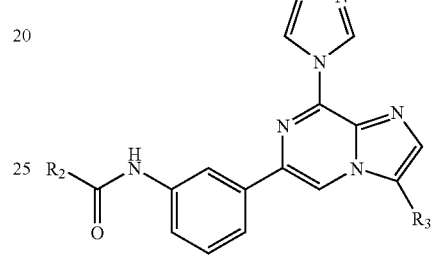
(Formula 10)

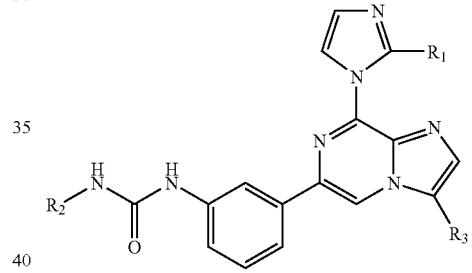
(Formula 11)

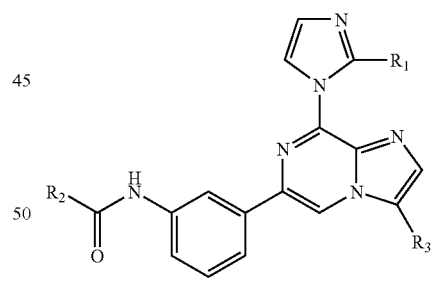
(Formula 12).

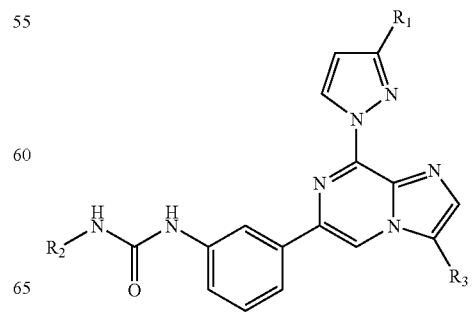
(Formula 13)

-continued

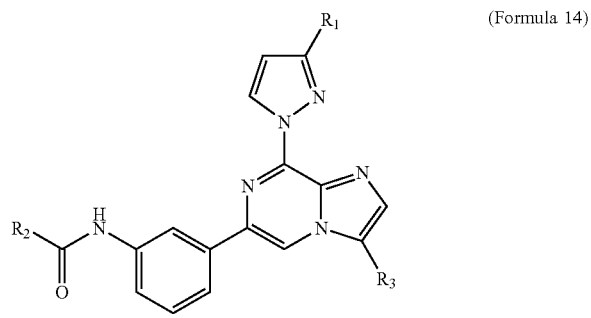

(Formula 14)

$R_1$, $R_2$, and $R_3$ shown in Formula 9 to Formula 14 may carry any of the definitions set forth above for these variables.

In some preferred embodiments the invention includes compounds and pharmaceutically acceptable forms, in which:

$R_1$ is bromo or $C_1$–$C_4$alkyl; or
$R_1$ is phenyl substituted with 0 to 2 substituents independently chosen from fluoro, chloro, bromo, $C_1$–$C_2$alkyl, and $C_1$–$C_2$alkoxy;
$R_2$ is phenyl or benzyl, each of which is substituted with 0 to 3 substituents independently chosen from: (i) hydroxy, halogen, amino, $C_1$–$C_2$haloalkyl, and $C_1$–$C_2$haloalkoxy; and (ii) $C_1$–$C_6$alkyl, $C_1$–$C_6$alkoxy, mono- and di-($C_1$–$C_4$alkyl)amino, mono- and di-($C_1$–$C_4$alkyl)amino($C_1$–$C_4$alkyl), piperazinyl ($C_0$–$C_1$alkyl), piperidinyl($C_0$–$C_1$alkyl) and morpholinyl($C_0$–$C_1$alkyl); each of which (ii) is substituted with 0 to 3 substituents independently chosen from halogen, hydroxy, amino, $C_1$–$C_2$alkoxy, and mono- and di-($C_1$–$C_4$alkyl)amino.
$R_3$ is hydrogen or $C_1$–$C_4$alkyl.

The definitions of the variables $R_1$, $R_2$, $R_3$, X, W, $Z_1$, and $Z_2$ given herein may be combined in any way that results in a stable compound of Formula I, 1, 1-A, or 2 to 14.

Certain compounds of Formula I described herein modulate kinase and/or Hsp90 complex activity. Certain preferred compounds of Formula I are highly active inhibitors of Hsp90 complex activity.

Modulation of kinase activity is determined by a biochemical assay such as the EphB4 biochemical assay of Example 8, or the c-Kit, TIE-2, and VEGF-$R_2$ assays of Example 9.

Inhibition of Hsp90 complex activity results in reduced cell proliferation. Thus, modulation of Hsp90 complex activity is determined by a cell proliferation assay such as the tumor cell proliferation assay of Example 11. Hsp90 complex activity inhibition may also be observed via Western blot, for example by the Western blot protocol of Example 10. In this protocol reduced level of Hsp90 substrate proteins, such as ErbB2, Raf, or Akt, indicates inhibition of Hsp90 complex activity.

The invention includes compounds of Formula I, which exhibit an $IC_{50}$ of 25 micromolar or less, and more preferably 10 micromolar or less in an in vitro assay of tumor cell proliferation (such as the assay of Example 11).

The invention includes a method of modulating binding of ATP to the Hsp90 complex, the method comprising contacting a cell or cells expressing Hsp90 complex with a compound of Formula I or any pharmaceutically acceptable form thereof according in an amount sufficient to detectably decrease the level of an Hsp90 complex substrate protein in vitro. Decreased level of Hsp90 complex substrate protein may be observed via Western blot, for example by the Western blot protocol of Example 10. The substrate may be ErbB2 or other Hsp90 complex substrate, such as Raf or Akt.

Modulation of ATP binding to Hsp90 complex may be in vivo or in vitro. Preferably the cell(s) expressing Hsp90 complex are present in a mammal. The mammal may be a human, companion animal, such as a cat or dog, livestock animal, or other mammal.

Pharmaceutical Preparations

Compounds, salts, and any other pharmaceutically acceptable forms of the invention can be administered as the neat chemical, but are preferably administered as a pharmaceutical composition or formulation. Accordingly, the invention provides pharmaceutical formulations comprising a compound or pharmaceutically acceptable form of Formula I, together with one or more pharmaceutically acceptable carriers, excipients, adjuvants, diluents, or other ingredients.

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder, or condition treated and may be empirically determined.

Compounds of general the invention may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75 % of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Preferred carriers for parenteral administration include propylene glycol, ethyl oleate, pyrrolidone, ethanol, and sesame oil.

Suppositories

Compounds of the invention may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye. Topical compositions of the present invention may be in any form including, for example, solutions, creams, ointments, gels, lotions, milks, cleansers, moisturizers, sprays, skin patches, and the like.

Such solutions maybe formulated as 0.01%–10% isotonic solutions, pH about 5–7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows: Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorption enhancers.

Pharmaceutical compositions of the invention may also contain additional active agents can be chosen from a wide variety of molecules, which can function in different ways to enhance the therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds, salts, or other pharmaceutically acceptable forms thereof, of the invention in a container and instructions for using the composition to treat an animal (typically a human patient) suffering from a disease or disorder responsive to kinase modulation or Hsp90 complex modulation, or prevent in a patient. Preferably the packaged pharmaceutical formulation contains instructions for using the composition to treat a patient suffering from a disease or disorder responsive to Hsp90 complex modulation.

The invention includes providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of the invention can be administered alone, as mixtures, or in combination with other active agents.

Methods of Treatment

The invention includes new imidazo[1,2-a]pyrazines. Certain compounds described herein are modulators of protein kinases, for example $EphB_4$, Tie-2, c-Kit, and VEGF-R2 kinases, and/or the Hsp90 complex. Certain preferred compounds described herein are highly active inhibitors of the Hsp90 complex. The compounds of the present invention are useful for the treatment of diseases and disorders responsive to kinase modulation and/or Hsp90 complex modulation. Preferred compounds described herein are useful for the treatment of diseases and disorders responsive to Hsp90 complex modulation.

Without wishing to be bound to any particular theory, it is believed that the interaction of the compounds of Formula I with one or more of several kinases or the Hsp90 complex results in the pharmaceutical utility of these compounds. It is believed that the interaction of certain preferred compounds of Formula I with the Hsp90 complex results in the pharmaceutical utility of these preferred compounds.

Accordingly, the invention includes a method of treating a mammal, preferably a human, having a disease or disorder responsive to kinase or Hsp90 complex modulation, comprising administrating to the mammal of an effective amount of a compound of Formula I.

Methods of treatment also include modulating kinase and/or Hsp90 complex activity, by inhibiting ATP binding or hydrolysis by a kinase or the Hsp90 complex or by some other mechanism, in vivo, in a patient suffering from a disease or disorder responsive to kinase or Hsp90 complex modulation, by administering a sufficient concentration of a compound of Formula I to inhibit kinase and/or Hsp90 complex activity in vitro. By "sufficient concentration" of a compound administered to the patient is meant the concentration of the compound available in the patient's system to combat the disease or disorder. Such a concentration be ascertained experimentally, for example by assaying blood concentration of the compound, or theoretically, by calculating bioavailability.

In a preferred embodiment, the invention includes a method of treating a patient suffering from a disease or disorder responsive to Hsp90 complex modulation, wherein the disease or disorder is cancer, a neurodegenerative disorder, an autoimmune disease, or inflammation.

The invention provides methods of treatment in which a compound of the invention is the only active agent given to a patient and also includes methods of treatment in which a compound of Formula I is given to a patient with one or more active agents.

Diseases and Disorders Responsive to Kinase Modulation

Certain compounds described herein are useful for treating a patient suffering from a disease or disorder responsive to kinase modulation.

Protein kinases, the largest family of human enzymes, are now considered to be the largest druggable target class. Encompassing well over 500 proteins (2% of the human genome), kinases play critical roles in signaling pathways controlling fundamental cellular processes such as proliferation, differentiation, and death (apoptosis). Abnormal kinase activity has been implicated in a wide range of diseases, including multiple cancers and autoimmune and inflammatory diseases. The multifaceted role of kinases in key cell signaling pathways provides a significant opportunity to identify novel drugs targeting kinases and signaling pathways. Accordingly, there is intense industry-wide interest in this target family, with kinase related research accounting for nearly 25% of the discovery programs at many pharmaceutical and biotechnology companies. The recently demonstrated efficacy of multiple kinase inhibitors in the treatment of cancer including the FDA approval of the kinase inhibitor GLEEVEC (imatinib mesylate), a c-Kit, PDGFR, and Abl kinase inhibitor, for the treatment of chronic myeloid leukemia, and the proof of clinical efficacy for AVASTIN, a VEGF modulator that inhibits angiogenesis, is testimony to the great clinical potential of kinase and other signal transduction inhibitors as therapeutics.

Kinases are implicated in a large variety of diseases, as certain mutations in protein kinases can lead to activation of pathways causing, for example, the production of tumors, while other mutations in protein kinases block pathways and prevent a response.

Altered PKA (cyclic AMP-dependent protein kinase) expression is implicated in a variety of disorders and diseases including cancer, thyroid disorders, diabetes, atherosclerosis, and cardiovascular disease. Altered MAP (mitogen-activated protein) kinase expression is implicated in a variety of disease conditions including cancer, inflammation, immune disorders, and disorders affecting growth and development. RTKs (receptor tyrosine kinases), CDKs and STKs (serine/threonine kinases) have all been implicated in a host of pathogenic conditions including, significantly, large number of diverse cancers. Others pathogenic conditions that have been associated with PTKs include, psoriasis, hepatic cirrhosis, diabetes, atherosclerosis, angiogenesis, restinosis, ocular diseases, rheumatoid arthritis and other inflammatory disorders, autoimmune disease, and a variety of renal disorders.

Within some embodiments the conditions, diseases and/or disorders that are affected using compounds of Formula I and compositions comprising such compounds include, but are not limited to, psoriasis, pathological angiogenesis, cancer (for example, chronic myelogenous leukemia, gastrointestinal stromal tumors, non-small cell lung cancer, breast cancer, ovarian cancer, recurrent ovarian cancer, prostate cancer such as hormonal refractory prostate cancer, kidney cancer, head and neck cancer, or colorectal cancer), immunoregulation (graft rejection), atherosclerosis, rheumatoid arthritis, Parkinson's disease, Alzheimer's disease, diabetes (for example insulin resistance or diabetic retinopathy), septic shock, and the like.

Certain kinase inhibitory compounds play an active role in angiogenesis certain compounds described herein are useful for modulating angiogenesis. Angiogenesis, the formation of new blood vessels from preexisting ones, plays a critical role in many pathological settings, including cancer, chronic inflammation, diabetic retinopathy and macular degeneration. Angiogenesis is regulated by multiple cell-signaling pathways, including pathways controlled by cellular kinases. Blocking angiogenesis, through the modulation of cell kinases, therefore, represents an effective approach to the treatment of diseases such as cancer. Thus methods of treatment include administering a sufficient amount of a compound or form thereof of the invention to decrease the symptoms or slow the progression of these diseases or disorders by inhibiting the rate of angiogenesis in a tissue.

Diseases and Disorders Responsive to Hsp90 Complex Modulation

Certain compounds described herein are useful for treating a patient suffering from a disease or disorder responsive to Hsp90 complex modulation.

The Hsp90 complex and its substrate proteins, including Akt, ErbB2, and Raf, have been implicated in a number of cancerous conditions. Thus Hsp90 complex inhibitors of the invention are particularly useful in the treatment of cancer, including, but not limited to, chronic myeloid leukemia, melanoma, breast, ovarian, brain, lung, thyroid, colorectal, prostate, and bladder cancer. Because of the role of Hsp90 in modulating the cellular stress response Hsp90 inhibitors of the invention are also useful in the treatment of heart disease, stroke, and neurodegenerative diseases including multiple sclerosis, Alzheimer's dementia, and ischemic optic neuropathy. Thus methods of treatment include administering a sufficient amount of a compound or form thereof of the invention to decrease the symptoms or slow the progression of these diseases or disorders.

Combination Therapy

In addition to methods of treatment in which a compound of Formula I is the only active agent given to a patient, the invention further includes methods for combination drug therapy, in which a compound of the invention is given to a patient together with one or more other active agents. Thus in one embodiment the invention provides a method of treating cancer, which comprises administering to a mammal in need thereof an effective amount of a compound of Formula I together with a second active agent, which is useful for treating cancer. For example the second agent may be an antitumor agent. Treatment with the second active agent may be prior to, concomitant with, or following treatment with a compound of Formula I. In certain embodiments a compound of Formula I is combined with another active agent in a single dosage form. Suitable antitumor therapeutics that may be used in combination with a compound of Formula I include, but are not limited to chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Dosage Levels

Dosage levels of the order of from about 0.1 mg to about 140 mg per kilogram of body weight per day are useful in the treatment of the conditions listed above (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

EXAMPLES

The invention is illustrated by the following non-limiting examples. Exemplary syntheses of compounds of the Formula I are included in this section.

Example 1

Synthesis of 1-o-tolyl-3-{3-[8-(4-p-tolyl-imidazol-1-yl)-imidazo[1,2-a]pyrazin-6-yl]-phenyl}-urea (Compound 6)

Step 1. Preparation of 6,8-dibromoimidazo[1,2-a]pyrazine (Compound 3)

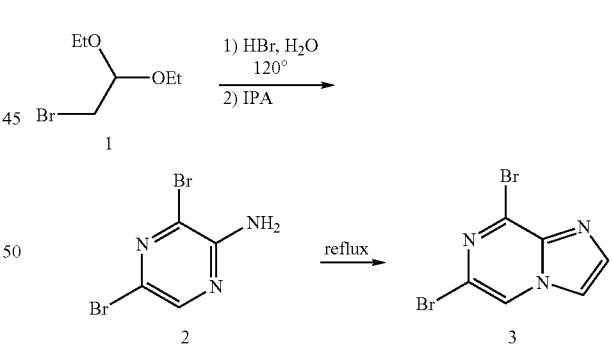

A mixture of bromoacetaldehyde diethyl acetal (1) (51 grams (g)), 48% hydrobromic acid (HBr) (11 milliliters (ml)), and water (11 ml) is heated at 120° C. for 1 hour (hr). The solution is cooled, poured into a mixture of sodium bicarbonate (NaHCO$_3$) (60 g), and isopropyl alcohol (IPA) (200 ml), and stirred for 0.5 hr. The mixture is filtered, and the filtrate treated with 3,5-dibromo-2-aminopyrazine (2) (33 g) and heated under reflux for 16 hr. The suspension is cooled in ice, treated with 48% HBr (3 ml) and diethyl ether (60 ml) and filtered to give (3) (33 g) as the hydrobromide salt.

Step 2. Preparation of 6-Bromo-8-(4-p-tolyl-imidazol-1-yl)-imidazo[1,2-a]pyrazine (Compound 4)

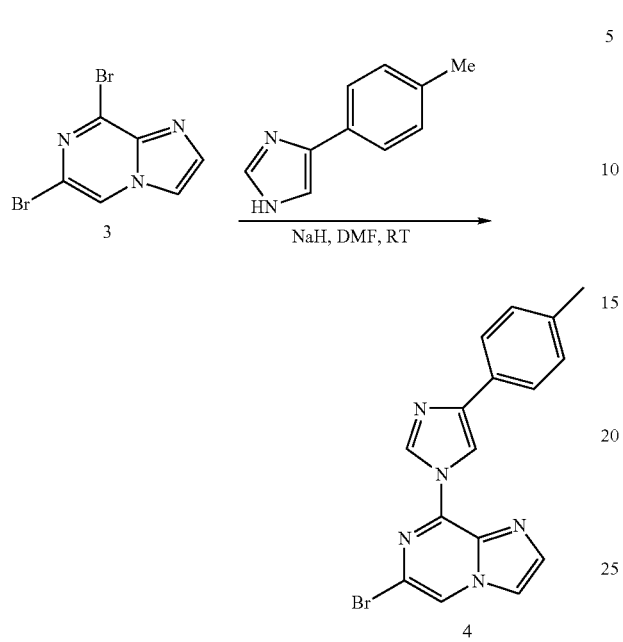

Sodium hydride (NaH) (144 milligrams (mg) of a 60% dispersion in mineral oil) is added to a solution of 4-p-tolyl-1H-imidazole (571 mg) in N,N,-dimethylformamide (DMF) (10 ml) and the mixture is stirred at room temperature (rt) for 0.5 hr. A solution of 6,8-dibromoimidazo[1,2-a]pyrazine (3) (1.0 g) in DMF (10 ml) is added. The mixture is stirred at room temperature (rt) for 16 hr. Water (50 ml) is added and the mixture is extracted with ethyl acetate (3×70 ml); extracts are washed with water (2×50 ml) and brine (1×50 ml), dried over magnesium sulfate ($MgSO_4$), and evaporated in vacuo to give a waxy solid. The solid is slurried with a little diethyl ether and filtered to give 6-Bromo-8-(4-p-tolyl-imidazol-1-yl)-imidazo[1,2-a]pyrazine (4) (1.08 g) as a light brown solid.

Step 3. Preparation of 3-[8-(4-p-Tolyl-imidazol-1-yl)-imidazo[1,2-a]pyrazin-6-yl]-phenylamine (Compound 5)

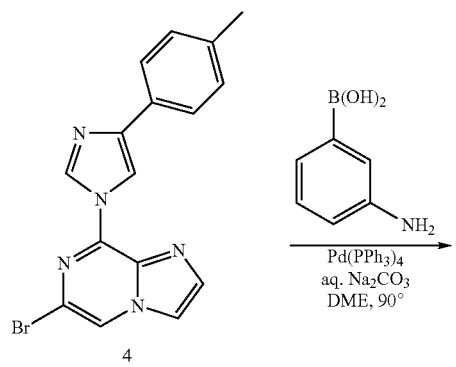

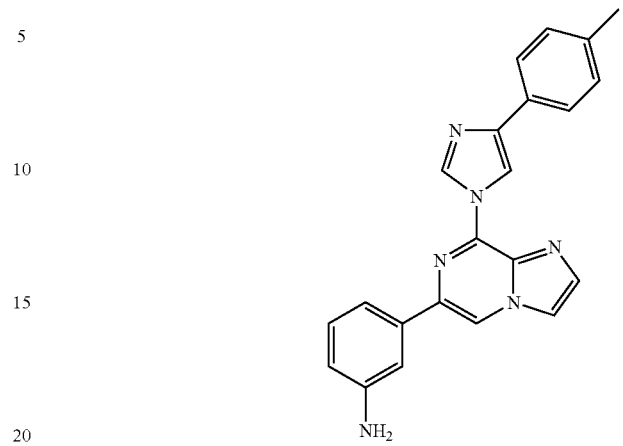

A mixture of 6-bromo-8-(4-p-tolyl-imidazol-1-yl)-imidazo[1,2-a]pyrazine (4) (870 mg), 3-aminophenylboronic acid hydrochloride (511 mg), tetrakis(triphenylphosphine) palladium ($Pd(PPh_3)_4$) (142 mg), 1 M aqueous sodium carbonate ($Na_2CO_3$) (7.4ml), and 1,2-dimethoxyethane (DME) (35 ml) is heated at 90° C. for 16 hours. The mixture is cooled to rt, treated with water (50 ml) and extracted with ethyl acetate (3×80 ml). The extracts are washed with water (1×50 ml) and brine (1×50 ml), dried over $MgSO_4$, and evaporated in vacuo to give a semi-solid which is triturated with diethyl ether/methanol (10:1) to give 3-[8-(4-p-Tolyl-imidazol-1-yl)-imidazo[1,2-a]pyrazin-6-yl]-phenylamine (5) (600 mg) as a cream-colored solid.

Step 4. Preparation of 1-o-Tolyl-3-{3-[8-(4-p-tolyl-imidazol-1-yl)-imidazo[1,2-a]pyrazin-6-yl]-phenyl}-urea (Compound 6)

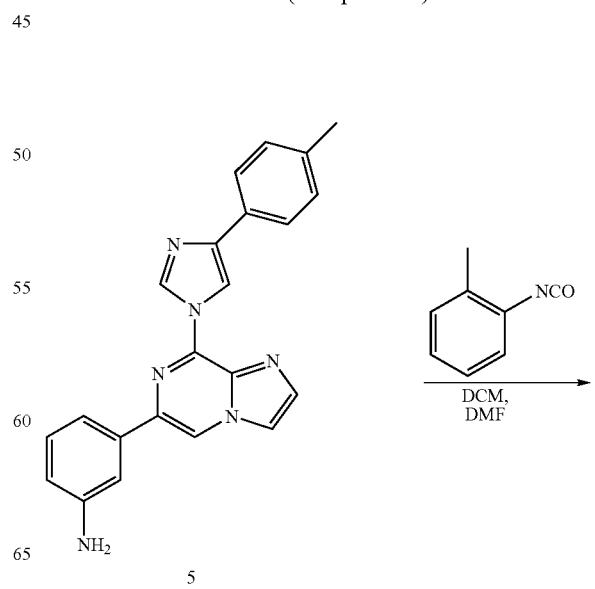

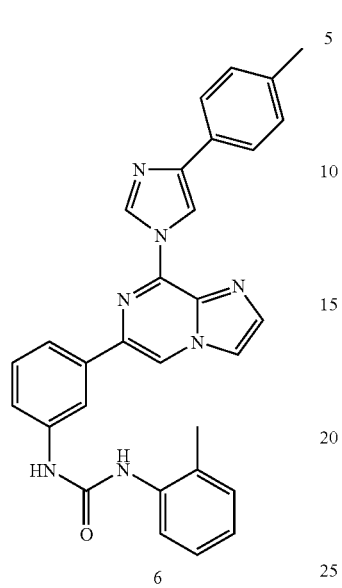

A solution of 3-[8-(4-p-tolyl-imidazol-1-yl)-imidazo[1,2-a]pyrazin-6-yl]-phenylamine (5) (50 mg), 1-isocyanato-2-methyl-benzene (18 mg), in dichloromethane (DCM) (3 ml) and DMF (0.5 ml) is stirred at room temperature for 16 hr. The mixture is concentrated in vacuo, the residue slurried with diethyl ether/methanol (20:1), and filtered to give 1-o-tolyl-3-{3-[8-(4-p-tolyl-imidazol-1-yl)-imidazo[1,2-a]pyrazin-6-yl]-phenyl}-urea (6) (40 mg) as a cream solid.

Example 2

Preparation of 2-(4-Chloro-phenyl)-N-{3-[8-(2-phenyl-imidazol-1-yl)-imidazo[1,2-a]pyrazin-6-yl]-phenyl}-acetamide

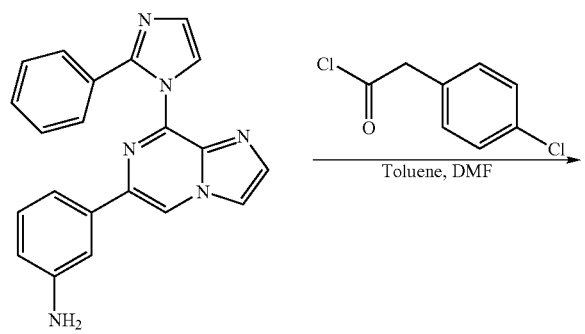

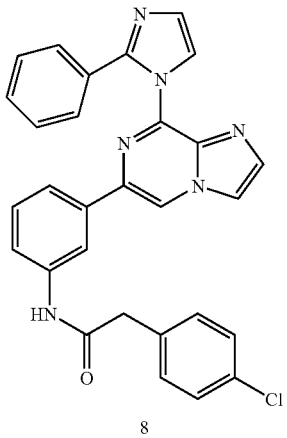

Solid 3-[8-(2-Phenyl-imidazol-1-yl)-imidazo[1,2-a]Pyrazin-6-yl]-phenylamine (50 mg) (7) is added to an anhydrous 0.2 M solution of (4-Chloro-phenyl)-acetyl chloride in toluene (0.7 mL) at room temperature, and 0.25 ml of anhydrous DMF is subsequently added to solubilize the reagents. The reaction is warmed to 50° C. and stirred under $N_2$ for 3 hours. The reaction is cooled to room temperature. Diethyl ether (15 ml) is then added slowly and the resulting tan solid 2-(4-Chloro-phenyl)-N-{3-[8-(2-phenyl-imidazol-1-yl)-imidazo[1,2-a]pyrazin-6-yl]-phenyl}-acetamide (60 mg) (8) is filtered and washed with diethyl ether and dried under vacuum.

Example 3

Additional Cell Proliferation Inhibitors

The following compounds are synthesized via the procedure set forth in Examples 1 and 2. In some instances changes in starting materials and reaction conditions that will be readily apparent to those skilled in the art of organic synthesis may be required.

LC-MS data reported in this example is obtained as follows:

LC conditions: RP-HPLC is performed on an AGILENT 1100 Binary HPLC system. The column is a Restek Ultra IBD 5 μm 1.0×30 mm (Cat. #: 9175331). The Mobile Phase contains component A, 0.2% Formic Acid/Water), and component B, Acetonitrile. The following Gradient is used:

| Time (min.) | % B | Flow Rate (μl/min) |
|---|---|---|
| 0 | 10 | 500 |
| 1.8 | 60 | 500 |
| 2.0 | 95 | 500 |
| 2.2 | 95 | 500 |
| 2.4 | 10 | 500 |

MS conditions: Electrospray MS is performed on a MICROMASS LCT equipped with a LockSpray source for accurate mass measurements. Spectra are acquired in positive ion mode from 100–1000 Da at an acquisition rate of 1 spectrum/0.9 s with a 0.1 s interscan delay. The instrument is tuned for a resolution of 5000 (FWHM). Every 5th scan is taken from the reference position of the Lockspray source. Leucine enkephalin (556.2771 [M+H]$^+$) is used as the reference, or lock mass.

| CPD # | Structure | Name | M + H | RT |
|---|---|---|---|---|
| 9 | 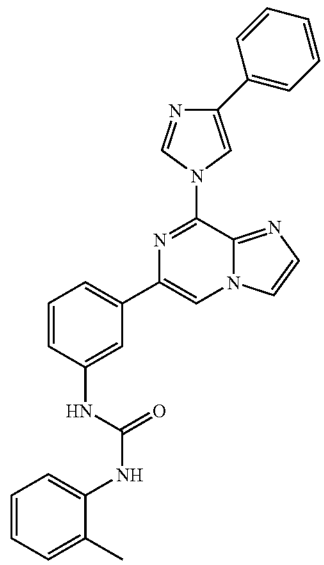 | 1-{3-[8-(4-Phenyl-imidazol-1-yl)-imidazo[1,2-a]pyrazin-6-yl]-phenyl}-3-o-tolyl-urea | 486.02 | 2.15 |
| 10 | 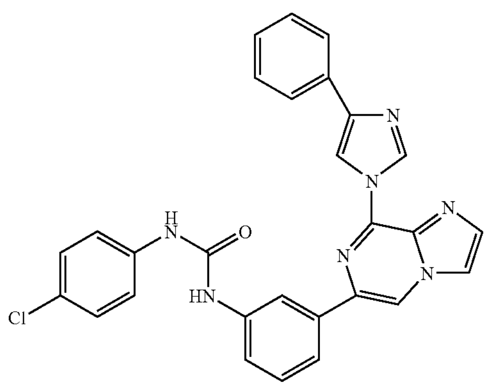 | 1-(4-Chloro-phenyl)-3-{3-[8-(4-phenyl-imidazol-1-yl)-imidazo[1,2-a]pyrazin-6-yl]-phenyl}-urea | 505.98 | 2.29 |
| 11 | 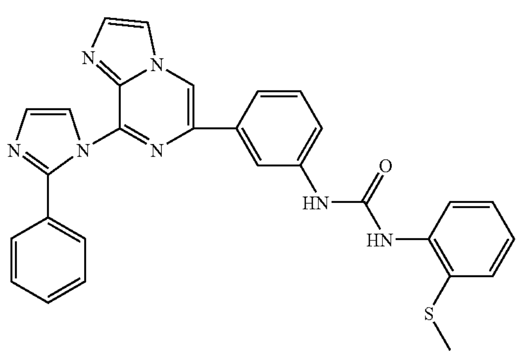 | 1-(2-Methylsulfanyl-phenyl)-3-{3-[8-(2-phenyl-imidazol-1-yl)-imidazo[1,2-a]pyrazin-6-yl]-phenyl}-urea | 517.97 | 1.43 |

-continued

| CPD # | Structure | Name | M + H | RT |
|---|---|---|---|---|
| 12 | 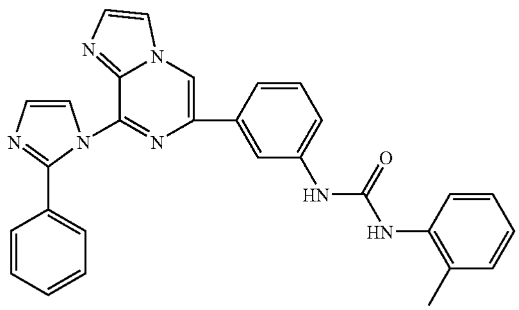 | 1-{3-[8-(2-Phenyl-imidazol-1-yl)-imidazo[1,2-a]pyrazin-6-yl]-phenyl}-3-o-tolyl-urea | 486.03 | 1.30 |
| 13 | 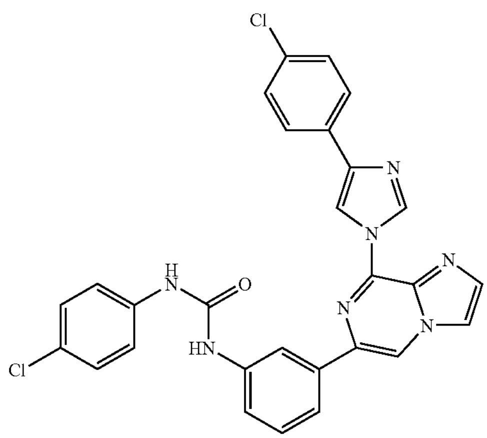 | 1-(4-Chloro-phenyl)-3-(3-{8-[4-(4-chloro-phenyl)-imidazol-1-yl]-imidazo[1,2-a]pyrazin-6-yl}-phenyl)-urea | 539.97 | 2.42 |
| 14 | 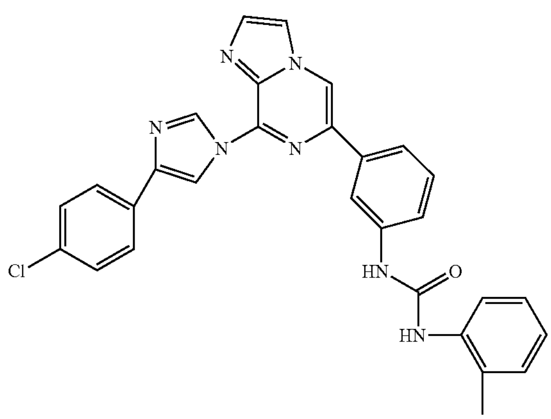 | 1-(3-{8-[4-(4-Chloro-phenyl)-imidazol-1-yl]-imidazo[1,2-a]pyrazin-6-yl}-phenyl)-3-o-tolyl-urea | 520.04 | 2.25 |
| 15 | 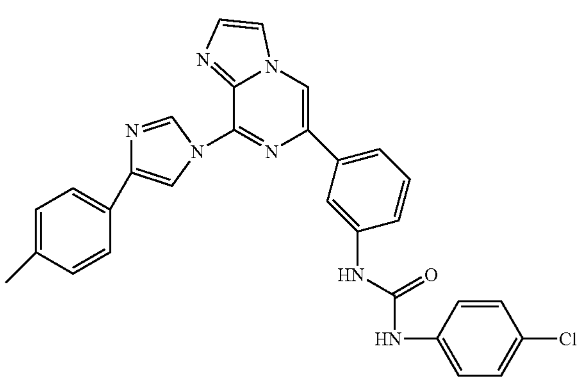 | 1-(4-Chloro-phenyl)-3-{3-[8-(4-p-tolyl-imidazol-1-yl)-imidazo[1,2-a]pyrazin-6-yl]-phenyl}-urea | 520.02 | 1.96 |

-continued

| CPD # | Structure | Name | M + H | RT |
|---|---|---|---|---|
| 16 | 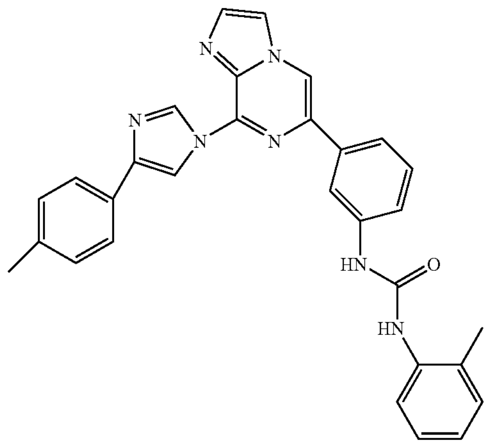 | 1-o-Tolyl-3-{3-[8-(4-p-tolyl-imidazol-1-yl)-imidazo[1,2-a]pyrazin-6-yl]-phenyl}-urea | 500.09 | 1.83 |
| 17 | 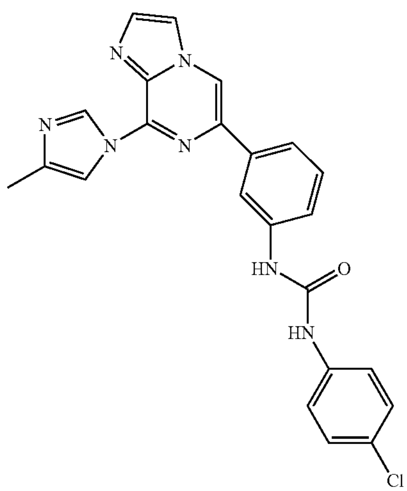 | 1-(4-Chloro-phenyl)-3-{3-[8-(4-methyl-imidazol-1-yl)-imidazo[1,2-a]pyrazin-6-yl]-phenyl}-urea | 444.26 | 1.49 |
| 18 | 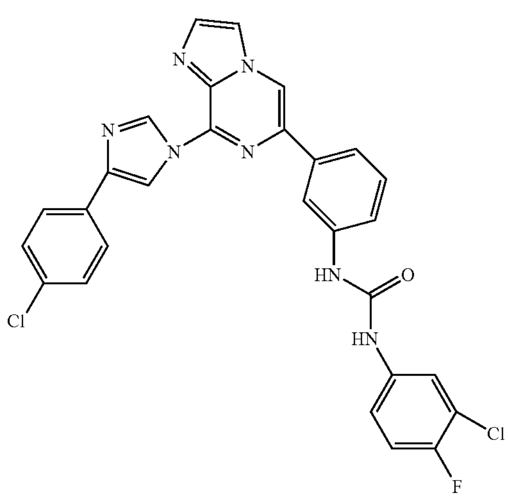 | 1-(3-Chloro-4-fluoro-phenyl)-3-(3-{8-[4-(4-chloro-phenyl)-imidazol-1-yl]-imidazo[1,2-a]pyrazin-6-yl}-phenyl) urea | 558.1 | 2.24 |

-continued

| CPD # | Structure | Name | M + H | RT |
|---|---|---|---|---|
| 19 | 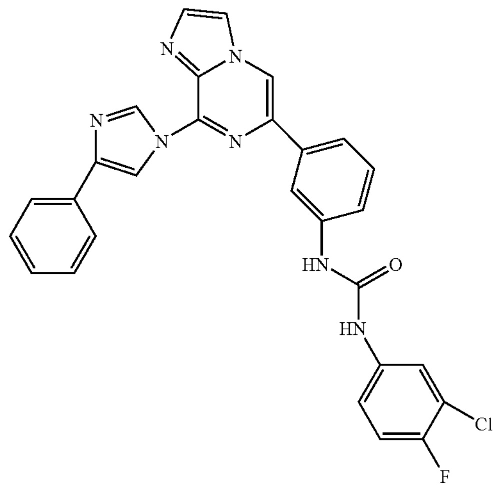 | 1-(3-Chloro-4-fluoro-phenyl)-3-{3-[8-(4-phenyl-imidazol-1-yl)-imidazo[1,2-a]pyrazin-6-yl]-phenyl}-urea | 524.07 | 2.02 |
| 20 | 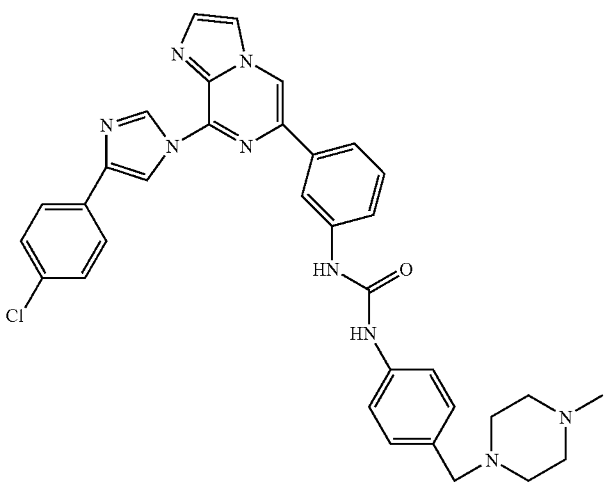 | 1-(3-{8-[4-(4-Chloro-phenyl)-imidazol-1-yl]-imidazo[1,2-a]pyrazin-6-yl}-phenyl)-3-[4-(4-methyl-piperazin-1-ylmethyl)-phenyl]-urea | 618.16 | 1.37 |
| 21 | 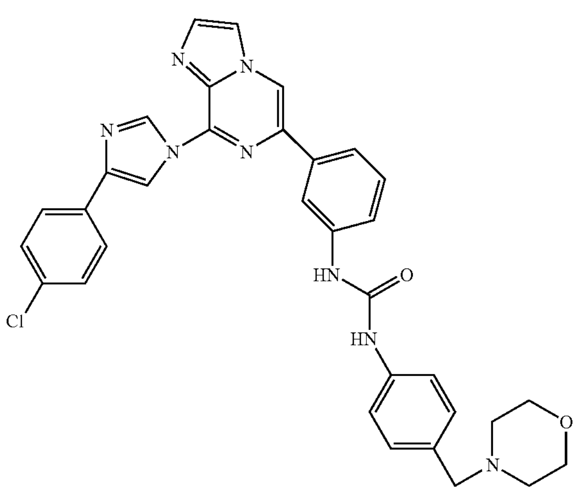 | 1-(3-{8-[4-(4-Chloro-phenyl)-imidazol-1-yl]-imidazo[1,2-a]pyrazin-6-yl}-phenyl)-3-(4-morpholin-4-ylmethyl-phenyl)-urea | 604.96 | 1.40 |

-continued

| CPD # | Structure | Name | M + H | RT |
|---|---|---|---|---|
| 22 | 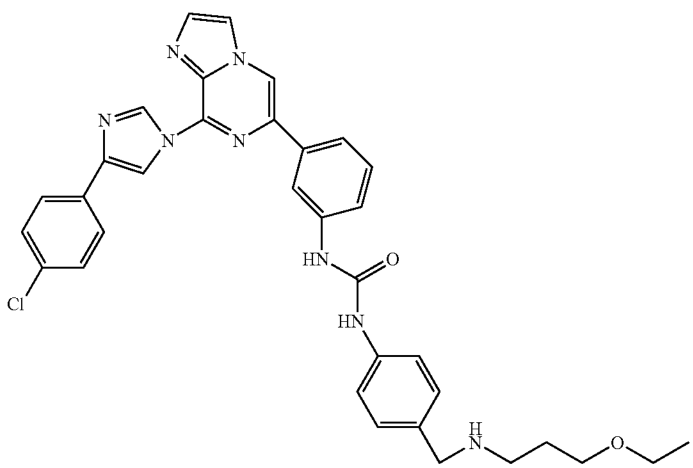 | 1-(3-{8-[4-(4-Chloro-phenyl)-imidazol-1-yl]-imidazo[1,2-a]pyrazin-6-yl}-phenyl)-3-{4-[(3-ethoxy-propylamino)-methyl]-phenyl}-urea | 620.99 | 1.55 |
| 23 | 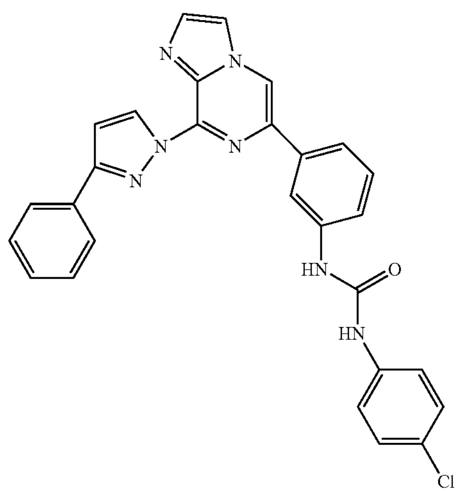 | 1-(4-Chloro-phenyl)-3-{3-[8-(3-phenyl-pyrazol-1-yl)-imidazo[1,2-a]pyrazin-6-yl]-phenyl}-urea | 505.91 | 1.67 |
| 24 | 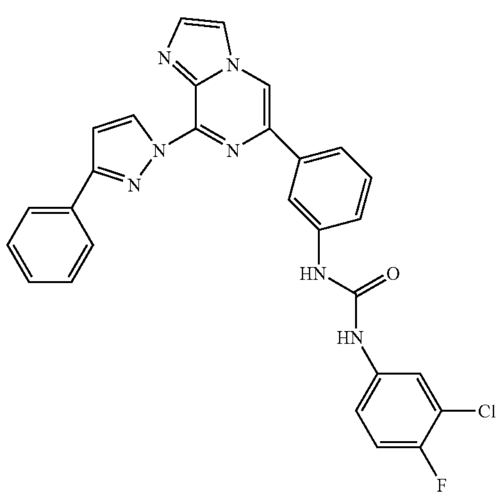 | 1-(3-Chloro-4-fluoro-phenyl)-3-{3-[8-(3-phenyl-pyrazol-1-yl)-imidazo[1,2-a]pyrazin-6-yl]-phenyl}-urea | 523.92 | 1.70 |

-continued

| CPD # | Structure | Name | M + H | RT |
|---|---|---|---|---|
| 25 | 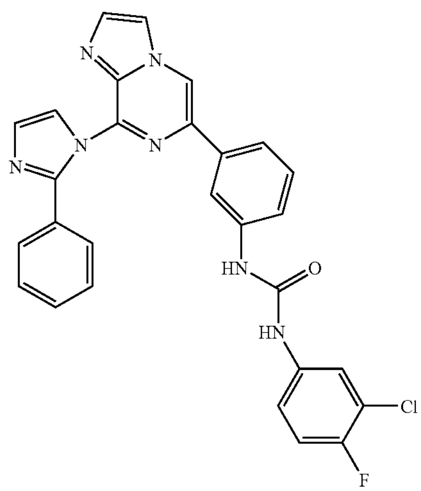 | 1-(3-Chloro-4-fluoro-phenyl)-3-{3-[8-(2-phenyl-imidazol-1-yl)-imidazo[1,2-a]pyrazin-6-yl]-phenyl}-urea | 524.13 | 1.30 |
| 26 | 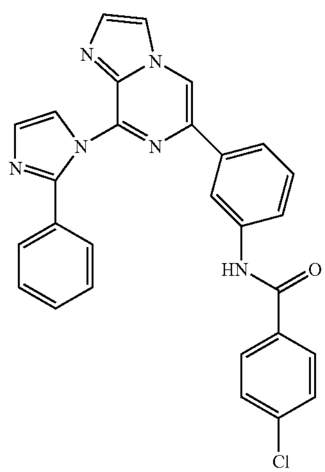 | 4-Chloro-N-{3-[8-(2-phenyl-imidazol-1-yl)-imidazo[1,2-a]pyrazin-6-yl]-phenyl}-benzamide | 491.11 | 1.15 |
| 27 | 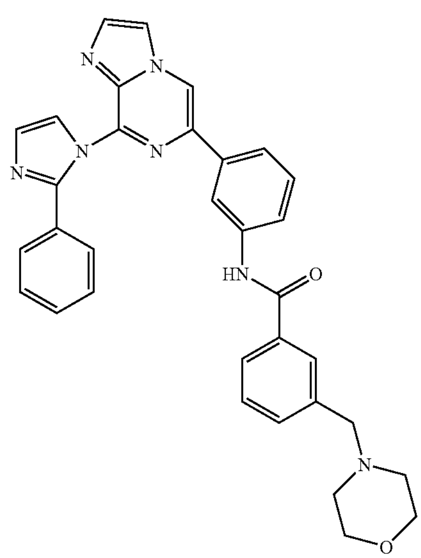 | 3-Morpholin-4-ylmethyl-N-{3-[8-(2-phenyl-imidazol-1-yl)-imidazo[1,2-a]pyrazin-6-yl]-phenyl}-benzamide | 556.22 | 0.29 |

-continued

| CPD # | Structure | Name | M + H | RT |
|---|---|---|---|---|
| 28 | 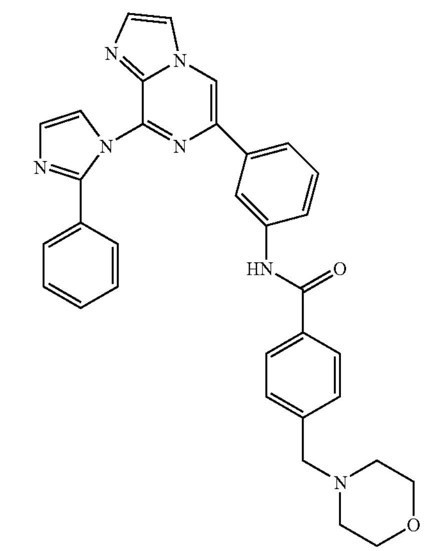 | 4-Morpholin-4-ylmethyl-N-{3-[8-(2-phenyl-imidazol-1-yl)-imidazo[1,2-a]pyrazin-6-yl]-phenyl}-benzamide | 556.24 | 0.29 |
| 29 | 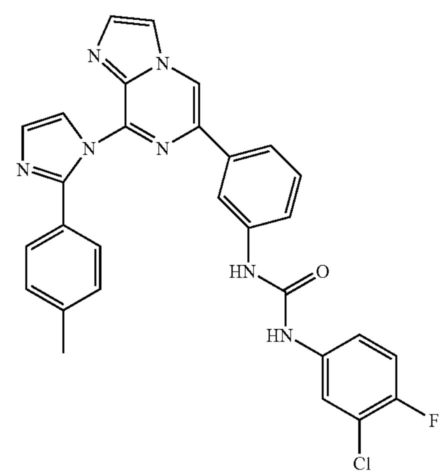 | 1-(3-Chloro-4-fluoro-phenyl)-3-{3-[8-(2-p-tolyl-imidazol-1-yl)-imidazo[1,2-a]pyrazin-6-yl]-phenyl}-urea | 538.17 | 1.55 |
| 30 | 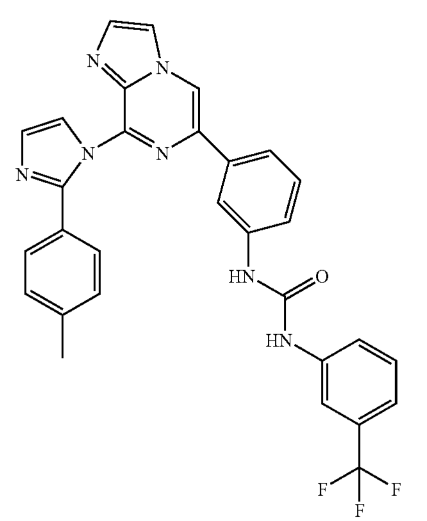 | 1-{3-[8-(2-p-Tolyl-imidazol-1-yl)-imidazo[1,2-a]pyrazin-6-yl]-phenyl}-3-(3-trifluoromethyl-phenyl)-urea | 554.18 | 1.07 |

-continued

| CPD # | Structure | Name | M + H | RT |
|---|---|---|---|---|
| 31 | 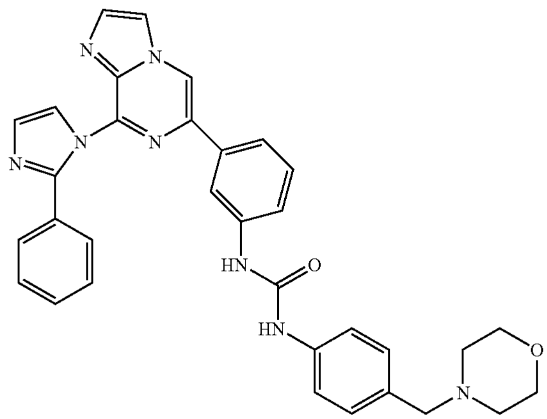 | 1-(4-Morpholin-4-ylmethyl-phenyl)-3-{3-[8-(2-phenyl-imidazol-1-yl)-imidazo[1,2-a]pyrazin-6-yl]-phenyl}-urea | 571.27 | 0.29 |
| 32 | 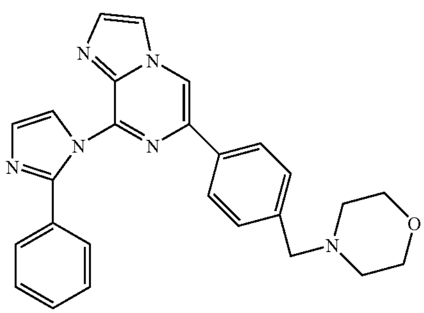 | 6-(4-Morpholin-4-ylmethyl-phenyl)-8-(2-phenyl-imidazol-1-yl)-imidazo[1,2-a]pyrazine | 437.22 | 0.29 |
| 33 | 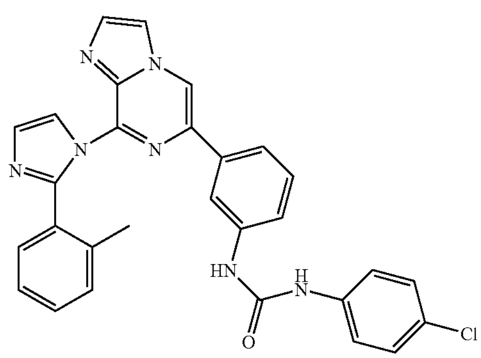 | 1-(4-Chloro-phenyl)-3-{3-[8-(2-o-tolyl-imidazol-1-yl)-imidazo[1,2-a]pyrazin-6-yl]-phenyl}-urea | 520.31 | 1.58 |
| 34 | 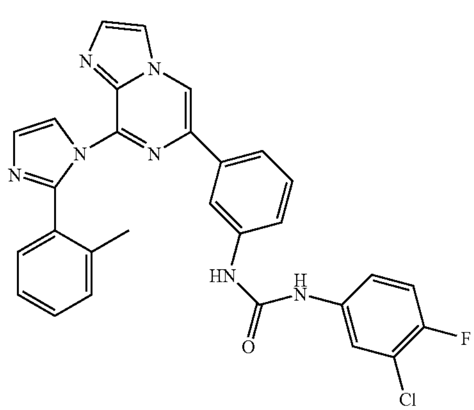 | 1-(3-Chloro-4-fluoro-phenyl)-3-{3-[8-(2-o-tolyl-imidazol-1-yl)-imidazo[1,2-a]pyrazin-6-yl]-phenyl}-urea | 538.16 | 1.10 |

-continued

| CPD # | Structure | Name | M + H | RT |
|---|---|---|---|---|
| 35 | 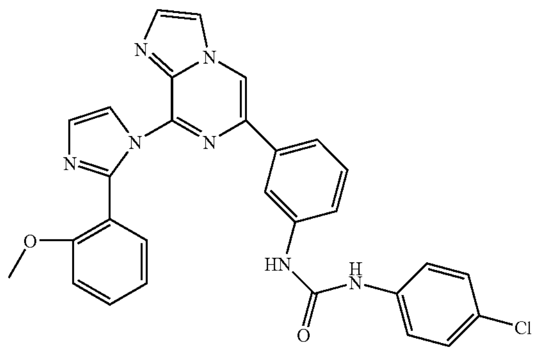 | 1-(4-Chloro-phenyl)-3-(3-{8-[2-(2-methoxy-phenyl)-imidazol-1-yl]-imidazo[1,2-a]pyrazin-6-yl}-phenyl)-urea | 536.13 | 0.90 |
| 36 | 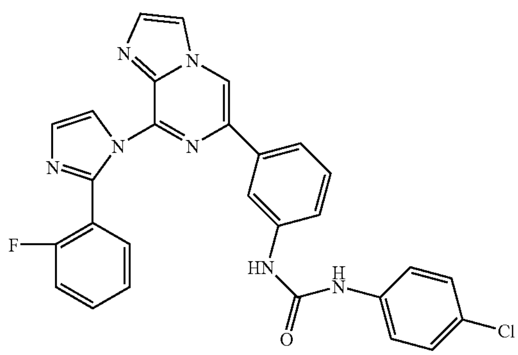 | 1-(4-Chloro-phenyl)-3-(3-{8-[2-(2-fluoro-phenyl)-imidazol-1-yl]-imidazo[1,2-a]pyrazin-6-yl}-phenyl)-urea | 524.13 | 1.25 |
| 37 | 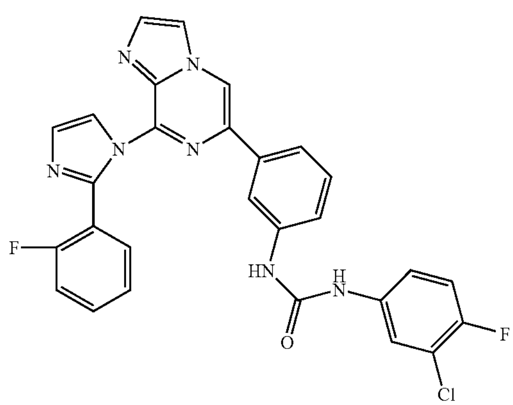 | 1-(3-Chloro-4-fluoro-phenyl)-3-(3-{8-[2-(2-fluoro-phenyl)-imidazol-1-yl]-imidazo[1,2-a]pyrazin-6-yl}-phenyl)-urea | 542.07 | 1.27 |
| 38 | 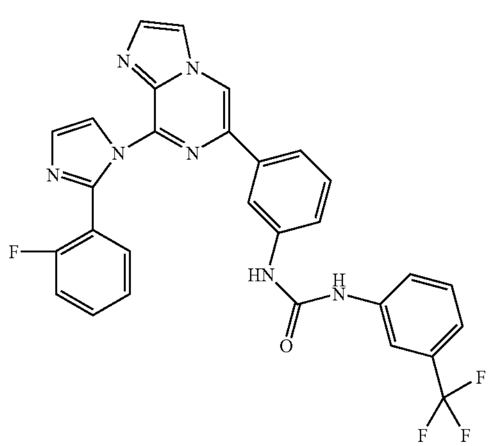 | 1-(3-{8-[2-(2-Fluoro-phenyl)-imidazol-1-yl]-imidazo[1,2-a]pyrazin-6-yl}-phenyl)-3-(3-trifluoromethyl-phenyl)-urea | 558.09 | 1.30 |

| CPD # | Structure | Name | M + H | RT |
|---|---|---|---|---|
| 39 | 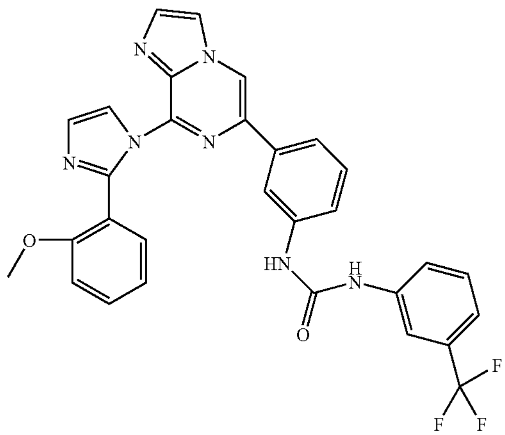 | 1-(3-{8-[2-(2-Methoxy-phenyl)-imidazol-1-yl]-imidazo[1,2-a]pyrazin-6-yl}-phenyl)-3-(3-trifluoromethyl-phenyl)-urea | 570.18 | 0.99 |
| 40 | 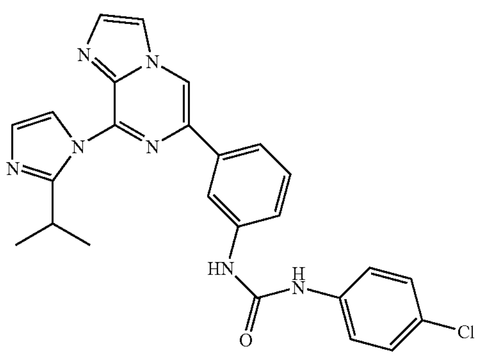 | 1-(4-Chloro-phenyl)-3-{3-[8-(2-isopropyl-imidazol-1-yl)-imidazo[1,2-a]pyrazin-6-yl]-phenyl}-urea | 472.12 | 1.34 |
| 41 | 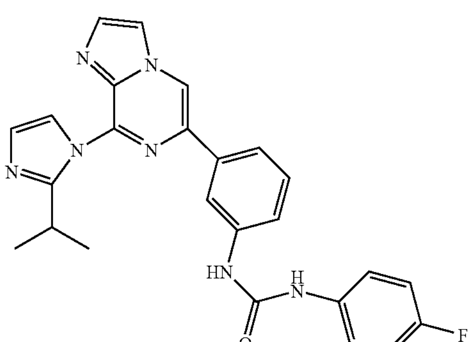 | 1-(3-Chloro-4-fluoro-phenyl)-3-{3-[8-(2-isopropyl-imidazol-1-yl)-imidazo[1,2-a]pyrazin-6-yl]-phenyl}-urea | 490.12 | 1.36 |

| CPD # | Structure | Name | M + H | RT |
|---|---|---|---|---|
| 42 | 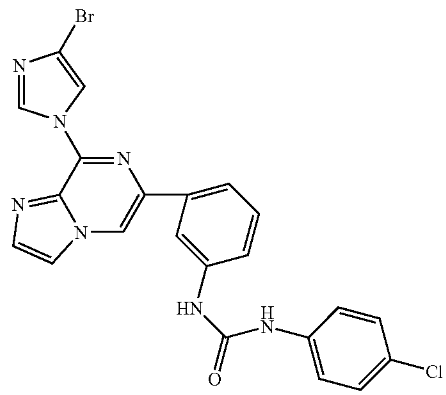 | 1-{3-[8-(4-Bromo-imidazol-1-yl)-imidazo[1,2-a]pyrazin-6-yl]-phenyl}-3-(4-chloro-phenyl)-urea | 507.99 | 1.89 |
| 43 | 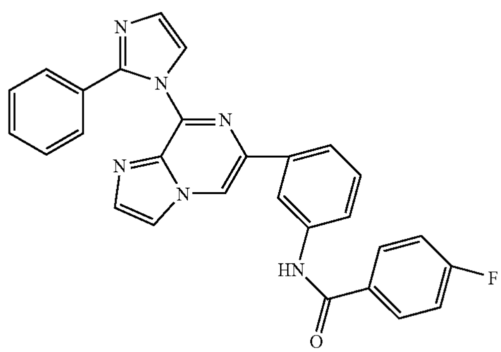 | 4-Fluoro-N-{3-[8-(2-phenyl-imidazol-1-yl)-imidazo[1,2-a]pyrazin-6-yl]-phenyl}-benzamide | 475.08 | 0.41 |
| 44 | 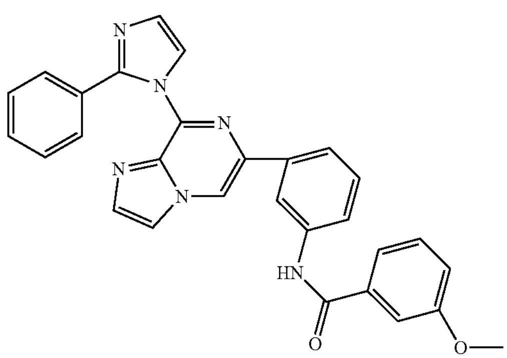 | 3-Methoxy-N-{3-[8-(2-phenyl-imidazol-1-yl)-imidazo[1,2-a]pyrazin-6-yl]-phenyl}-benzamide | 487.15 | 1.41 |
| 45 | 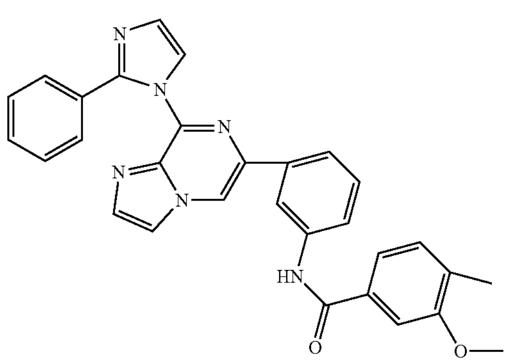 | 3-Methoxy-4-methyl-N-{3-[8-(2-phenyl-imidazol-1-yl)-imidazo[1,2-a]pyrazin-6-yl]-phenyl}-benzamide | 501.18 | 1.46 |

| CPD # | Structure | Name | M + H | RT |
|---|---|---|---|---|
| 46 | 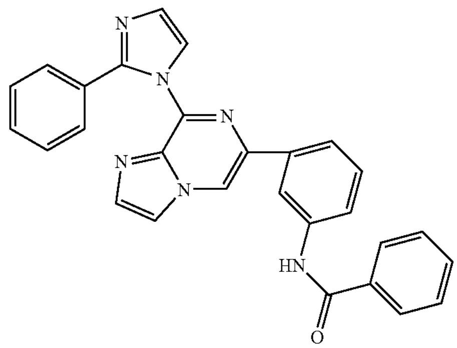 | N-{3-[8-(2-Phenyl-imidazol-1-yl)-imidazo[1,2-a]pyrazin-6-yl]-phenyl}-benzamide | 457.2 | 1.48 |
| 47 | 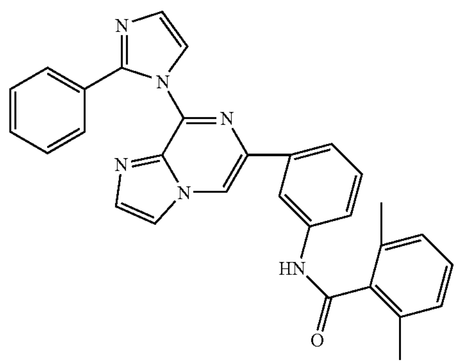 | 2,6-Dimethyl-N-{3-[8-(2-phenyl-imidazol-1-yl)-imidazo[1,2-a]pyrazin-6-yl]-phenyl}-benzamide | 485.22 | 1.24 |
| 48 | 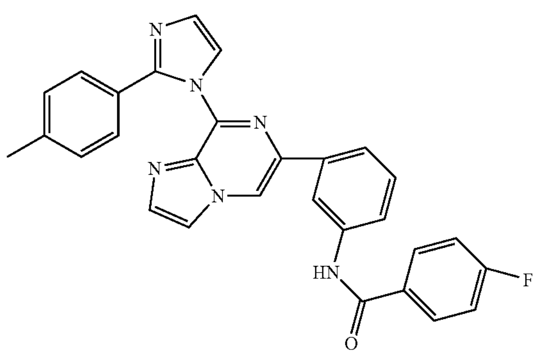 | 4-Fluoro-N-{3-[8-(2-p-tolyl-imidazol-1-yl)-imidazo[1,2-a]pyrazin-6-yl]-phenyl}-benzamide | 489.16 | 0.32 |
| 49 | 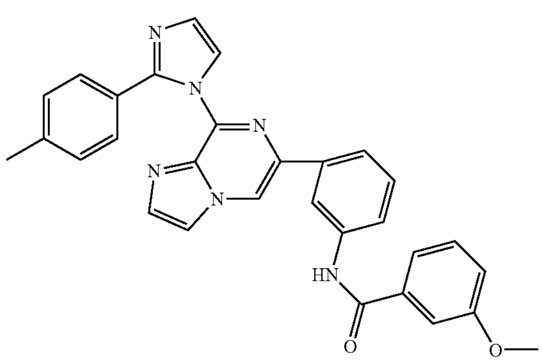 | 3-Methoxy-N-{3-[8-(2-p-tolyl-imidazol-1-yl)-imidazo[1,2-a]pyrazin-6-yl]-phenyl}-benzamide | 501.12 | 1.42 |

-continued

| CPD # | Structure | Name | M + H | RT |
|---|---|---|---|---|
| 50 | 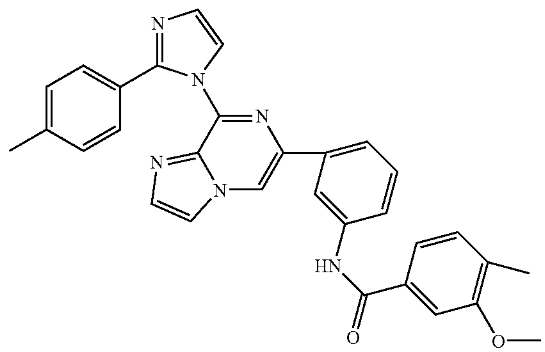 | 3-Methoxy-4-methyl-N-{3-[8-(2-p-tolyl-imidazol-1-yl)-imidazo[1,2-a]pyrazin-6-yl]-phenyl}-benzamide | 515.12 | 1.49 |
| 51 | 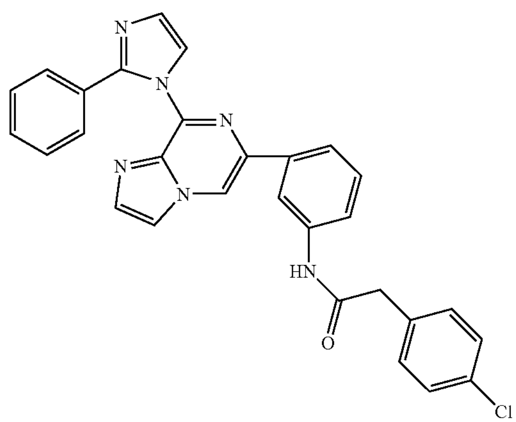 | 2-(4-Chloro-phenyl)-N-{3-[8-(2-phenyl-imidazol-1-yl)-imidazo[1,2-a]pyrazin-6-yl]-phenyl}-acetamide | 505.1 | 1.43 |
| 52 | 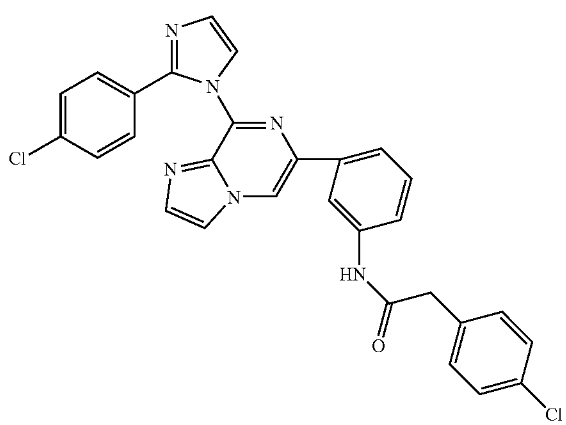 | 2-(4-Chloro-phenyl)-N-(3-{8-[2-(4-chloro-phenyl)-imidazol-1-yl]-imidazo[1,2-a]pyrazin-6-yl}-phenyl)-acetamide | 539.2 | 1.63 |

-continued

| CPD # | Structure | Name | M + H | RT |
|---|---|---|---|---|
| 53 | 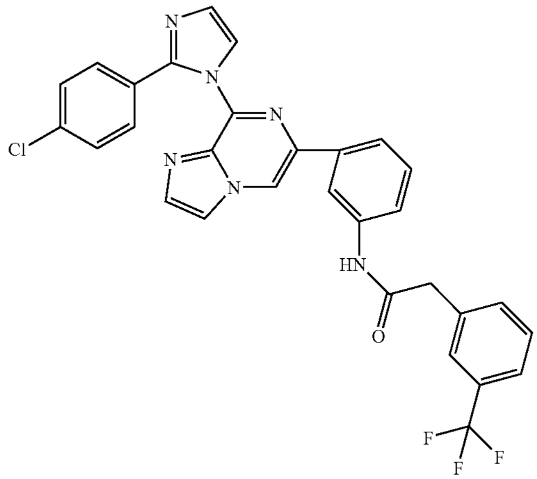 | N-(3-{8-[2-(4-Chloro-phenyl)-imidazol-1-yl]-imidazo[1,2-a]pyrazin-6-yl}-phenyl)-2-(3-trifluoromethyl-phenyl)-acetamide | 537.2 | 1.56 |
| 54 | 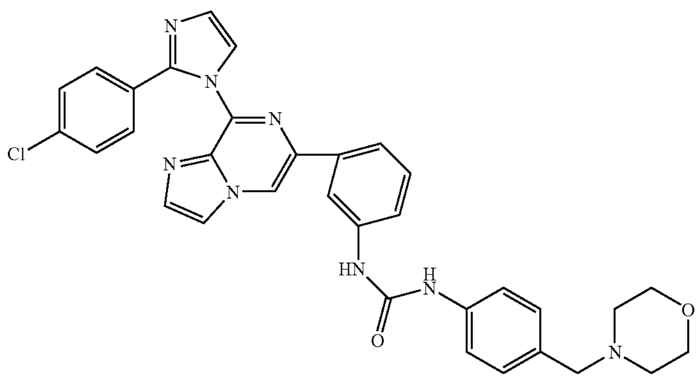 | 1-(3-{8-[2-(4-Chloro-phenyl)-imidazol-1-yl]-imidazo[1,2-a]pyrazin-6-yl}-phenyl)-3-(4-morpholin-4-ylmethyl-phenyl)-urea | 605.29 | 1.20 |
| 55 | 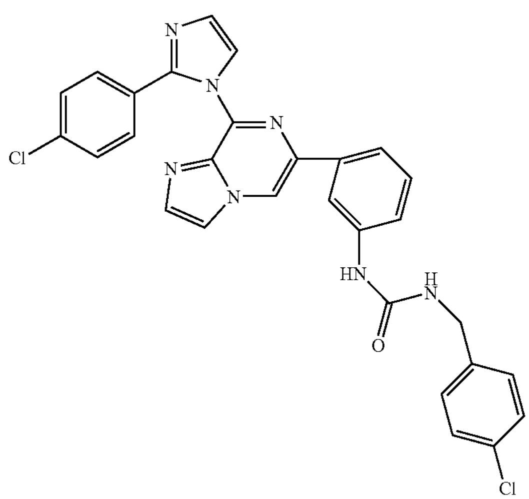 | 1-(4-Chloro-benzyl)-3-(3-{8-[2-(4-chloro-phenyl)-imidazol-1-yl]-imidazo[1,2-a]pyrazin-6-yl}-phenyl)-urea | 554.2 | 1.57 |

-continued

| CPD # | Structure | Name | M + H | RT |
|---|---|---|---|---|
| 56 | 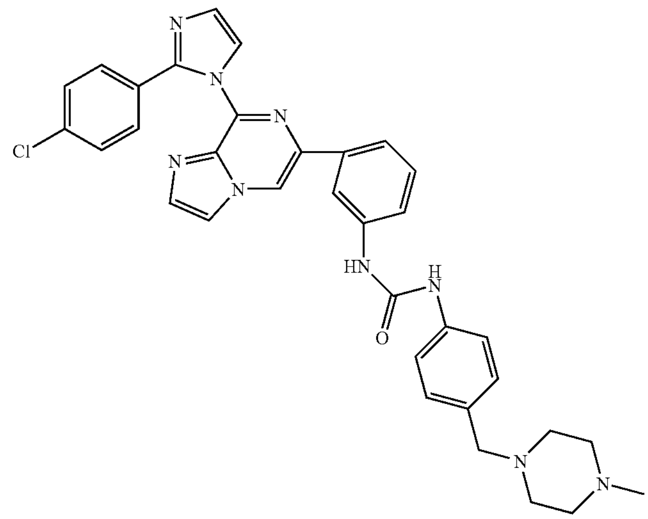 | 1-(3-{8-[2-(4-Chloro-phenyl)-imidazol-1-yl]-imidazo[1,2-a]pyrazin-6-yl}-phenyl)-3-[4-(4-methyl-piperazin-1-ylmethyl)-phenyl]-urea | 618.34 | 1.14 |

Example 4

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Radiolabeled probe compounds of the invention for use in positron emission tomography (PET) contain a positron emitting isotope such as $^{11}C$, $^{13}N$, $^{15}O$, or $^{18}F$. Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

Example 5

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 6

AKT-1 Kinase Assay

One standard AKT-1 Kinase Assay used to test compounds disclosed in this application is performed as follows.

Active recombinant N-terminus his-tagged AKT-1/PKBα kinase obtained from Sf21 cells (UBI # 14-276; 50–100 ng; 19–38 nM; about 4.5–9 mU) is incubated in 25 millimolar (mM) Tris pH 7.6; 5 mM Beta-glycerophosphate; 2 mM dithiothreitol (DTT); 100 micromolar (μM) sodium vanadate; and 10 mM magnesium chloride ($MgCl_2$). The final reaction volume is 40 microliters (μl). The reaction mixture is incubated in a 96-well Pierce REACTI-BIND streptavidin-coated high binding capacity coated white plate (Pierce # 15502) coated with saturating amounts of biotinylated Crosstide peptide (UBI #12-385; biotin-KGSGSGRPRTSS-FAEG (SEQ ID NO:1); 50 picomoles (pmoles); about 1.25 μM) and initiated with the addition of 2.5 microcurie (μCi) $^{32}P$-gamma-ATP (specific activity 3000 Ci/mmole; 10 mCi/ml; about 21 nanomolar (nM)). Compounds are initially tested in duplicate wells for determination of initial $IC_{50}$ inhibition in half log serial dilutions starting at 100 uM with a final concentration of 2% dimethyl sulfoxide (DMSO). Following a 30 min (minutes) incubation at 30° C., the reaction is stopped by aspiration tested 4×100 ul washes with TBS plus 0.05% Tween-20 prior to addition of 100 μl scintillant and counting in a Beckman TopCount instrument.

Percent inhibition is calculated as [1−((AVE $CPM_{compound}$−AVE $CPM_{no\ peptide\ background}$)/(AVE $CPM_{no\ compound\ MAX}$−AVE $CPM_{no\ peptide\ background}$))*100]. Staurosporine, a general ATP competitive kinase inhibitor is used as a reference compound. Staurosporine exhibits an $IC_{50}$ of approximately 60–100 nM for AKT-1 in the current assay format. Approximate S/N ratios are 8–12× with AVE CPM of Maximum about 15 k and no peptide background about 1.5 K. Improved S/N ratios can be obtained using higher amounts of either AKT-1 kinase or $^{32}$P-gamma-ATP. Cold ATP is not added in current format but has been added at up to 200 µM in the presence of 5 µCi $^{32}$P-γATP resulting in S/N ratios of approximately 5–10×.

Example 7

Second AKT-1 Kinase Assay

Another standard AKT-1 Kinase Assay used to test compounds disclosed in this application may be performed as follows.

Materials include: 96-well isoplates (Perkin-Elmer Corp., Cat.#1450-514) Biotinylated crosstide (Upstate Corp, Cat.#12-385), PKBα/AKT-1 (Panvera Corp., Cat# R3878), Adenosine 5'-triphosphate, [gamma-$^{32}$P] (Perkin Elmer Corp., Cat.# NEG302H001MC), and Streptavidin Coated Beads (Amersham Corp., Cat # RPNQ0007).

Kinase reaction buffer contains 3-[N-morpholino]propanesulfonic acid (MOPS) (4 mM), pH 7.2, beta-glycerol phosphate (5 mM), Ethylene glycol bis(2-aminoethylether)-N,N,N',N'-tetraaceticacid (EGTA) (1 mM), 0.2 mM sodium orthovanadate, 0.2 mM dithiothreitol, magnesium chloride (15 mM), crosstide (1.2 µM) and 135 ng/well AKT. Compounds in 2.5 µl of 100% DMSO are transferred to the assay plate, 37.5 µl of kinase in reaction buffer is added to the plate and 10 µl of a mixture of radioactive and non-radioactive ATP is added to achieve 5 µM total ATP and 0.2 µCi per well. The reactions are incubated at 24° C. for 45 min. and terminated by the addition of 200 µl of a stop solution. The stop solution contains 250 µg of SPA beads, 50 µM ATP, 5 mM ethylenediaminetetraacetic acid (EDTA), and 0.11% Triton X-100 in 1× PBS. The stopped reaction is incubated at 24 C for 30 min then centrifuged for 15 min at 800 rpms. Plates are counted in Microbeta Counter using the paralux counting method.

Example 8

Assay for EPHB$_4$ Kinase Activty

The following is a procedure for a standard biochemical assay for EphB$_4$ Kinase Activty.

Materials:
96-well, ½ area flat bottom, white polystyrene plates are purchased from Costar, cat #3693.
The cytoplasmic domain of recombinant EphB$_4$ kinase (amino acids 596–987, *Homo sapiens* EphB$_4$, GENBANK Accession No. AY056047.1) with a C-terminal 6× his tag is purified from Sf9 cells. Purity of >95% is assessed by Sypro-Ruby staining of SDS gels.
PTK Biotinylated Peptide Substrate 2, is purchased from Promega, cat #V288A.
LANCE Eu-W1024 labeled anti-phosphotyrosine antibody (PT66) is purchased from Perkin-Elmer, cat #AD0068. Kinase Buffer is purchased from Cell Signaling cat #9802.

Dilutions of compounds are made in 100% DMSO at 20× the final desired concentration. Compounds in 100% DMSO are transferred (1.25 µL) to the 96 well assay plate. A 18.75 µL volume of master mix containing the final concentrations (in 25 ul) of 0.01% BSA, 1× Cell Signaling Kinase Buffer, 0.5 µM PTK Biotinylated Peptide Substrate 2, and 60 ng/well of EphB$_4$ kinase is added to all wells, except the four negative control wells (which contain no kinase), and mixed. To initiate the reaction, 5 µL of 550 uM ATP is added to each well. (Final Concentration of ATP=110 µM). The reactions are incubated for 1 hour at room temperature (RT). After incubation a quantity of 8.35 µL of a 4×SA-APC Detection Mix is added to each well. The final concentration of Eu-labelled PT66 antibody is 1 nM and the SA-APC is 20 nM (based on the SA moiety). The reaction plates are incubated at RT for at least 15 minutes after SA-APC Detection Mix addition. The reaction plates are read on an Envision plate reader (Perkin-Elmer) with 605 nm Excitation and 605 nm and 640 nm Emission wavelengths. Values are corrected for the fluorescence in the absence of enzyme and inhibition curves are fit to the data using a Logit curve-fitting algorithm. IC$_{50}$ values are determined from these inhibition curves.

Example 9

Biochemical Assay

The following assay is a standard biochemical assay used to test activity of compounds as inhibitors of c-Kit, VEGF-R2, and Tie2 kinase activity.

Test compounds are diluted 1:20 from an original 20 µM DMSO stock and incubated with recombinant c-Kit (10 ng), Tie-2 (6 ng), or VEGF-R2 (1 ng) enzyme (ProQinase GmbH, Germany), biotinylated peptide (PTK peptide 2, Promega) in Cell Signalling kinase buffer (c-Kit and Tie-2) or Upstate Kinase buffer (VEGF-R2) and 5 ul of ATP (final concentrations: 50 µM (50 µM for the VEGF-R2 assay, 60 µM for the Tie2 assay, and 150 µM for the c-Kit assay) for 60 minutes at room temperature. The final assay volume is 25 µl. After the 60 minute incubation Streptavidin-APC Detection Mix, which includes 1 nM LANCE Eu-W1024 labeled anti-phosphotyrosine antibody PT66 (Perkin-Elmer, cat #AD0068) and 20 nM SA-APC (based on the SA moiety), is added. The reaction plates are incubated at room temperature for at least 15 minutes after SA-APC detection mix addition. The reaction plates are then read on an Envision plate reader (Perkin-Elmer) with 605 nm excitation 615 nM and 640 nm emission wavelengths.

For a negative control, i.e. a readout in which the kinases are not inhibited, the assay is run with without any test compound added. Staurosporine, a general kinase inhibitor, is used as a positive control.

IC$_{50}$ values are determined from an 11-point saturation binding curve for test compounds that show significant inhibition of one of the tyrosine kinases. In these assays concentration of test compound ranges from 10 µM to 20 nM. Equilibrium binding parameters are determined by fitting the allosteric Hill equation to the measured values with the aid of the computer program, such as FitP™ (BIOSOFT, Ferguson, Mo.).

Example 10

Western Blot

Tumor cells, such as MCF-7 or HCT-15 cells (both from ATCC, Manassas, Va.), are grown to ~50–70% confluency and are subsequently incubated for 4–48 hr at 37° C. in DMEM media containing 20 µM test compound. Cells are washed in ice-cold PBS, lysed, and spun at 10,000× g for 10 minutes to removes cellular debris. Protein concentration of the cleared lysates is determined using a commercially available protein assay, such as the Piece BCA assay. Equal protein amounts, approximately 30 µl/lane are loaded onto an SDS-PAGE gel. Proteins are transferred via electrophoresis to nitrocellulose membrane for western blotting. Blots are analyzed for depletion of an Hsp90 substrate protein, such as ErbB2 (Anti-ErbB2: Santa Cruz Biotechnology, Inc., #SC-284), Raf, or Akt, and increased levels of Hsp70 (Anti-HSP70, Transduction Labs #610608). An antibody against a protein that is not an Hsp90 client protein, such as PKA (Anti-PKA Transduction Labs #610980), is used as a loading control. Detection is via a horseradish peroxidase (HRP)-conjugated second antibody.

Example 11

Tumor Cell Monolayer Proliferation Assay

Test compounds are diluted to 1% DMSO, final concentration, and incubated with 3–5×10³ tumor cells (for example MCF-7 or HCT-15 cells) in a final volume of 200 µl for 5 days. CELLTITER 96 AQUEOUS ONE Solution Cell Proliferation Assay (Promega, Madison Wis.), a colorimetric assay for determining the number of viable cells is used to quantitate cell growth. In this method, 10–20 µl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

For saturation binding analysis cell proliferation is response to a range of test compound concentrations is determined, for example 6 or 11 concentrations test compound concentrations, from 10 µM to 20 nM may be used. Equilibrium binding parameters are determined by fitting the allosteric Hill equation to the measured values.

Example 12

Test Results

All compounds described in Examples 1–3 were tested in the assay of Example 11 found to exhibit an $IC_{50}$ of 25 micromolar or less. Certain compounds described herein exhibited an $IC_{50}$ of 10 micromolar or less, in the assay of Example 11.

All cited references are incorporated herein in their entirety. While preferred embodiments have been shown and described, various modifications and substitutions may be made thereto without departing from the spirit and scope of the invention.

What is claimed is:
1. A compound having Formula 1:

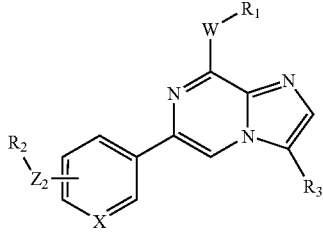

(Formula 1)

or pharmaceutically acceptable salt thereof, wherein:

$R_1$ is hydrogen, halogen, $C_1$–$C_7$alkyl, $C_1$–$C_6$alkoxy, $C_3$–$C_7$cycloalkyl($C_0$–$C_2$alkyl), heterocycloalkyl ($C_0$–$C_2$alkyl), sulfonamide, ($C_1$–$C_6$alkoxy)$C_1$–$C_6$alkyl, ($C_1$–$C_6$alkoxy)$C_1$–$C_6$alkoxy, mono- or di-($C_1$–$C_6$alkyl)amino, or mono- or di-($C_1$–$C_6$alkyl)amino ($C_1$–$C_6$alkyl); or $R_1$ is phenyl or phenyl fused to a 5 to 7-membered heterocycloalkyl ring containing 1 or 2 heteroatoms chosen from N, O, and S, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, $C_1$–$C_6$alkylthio, ($C_1$–$C_6$alkoxy) $C_1$–$C_6$alkyl, ($C_1$–$C_6$alkoxy)$C_1$–$C_6$alkoxy, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)$R_{13}$ where $R_{13}$ is $C_1$–$C_3$haloalkyl, phenyl, heterocycloalkyl, or heteroaryl;

W is phenyl or a 5- or 6-membered heteroaryl containing from 1 to 4 heteroatoms independently chosen from nitrogen, oxygen, and sulfur; wherein W is substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy) $C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl;

X is N or CH;

---

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Biotinylated Crosstide peptide

<400> SEQUENCE: 1

Lys Gly Ser Gly Ser Gly Arg Pro Arg Thr Ser Ser Phe Ala Glu Gly
1               5                   10                  15

$R_2$ is $C_1$–$C_7$alkyl, $C_3$–$C_7$cycloalkyl($C_0$–$C_2$alkyl), heterocycloalkyl($C_0$–$C_2$alkyl), $C_1$–$C_6$alkoxy, ($C_1$–$C_6$alkoxy)$C_1$–$C_6$alkyl, or ($C_1$–$C_6$alkoxy)$C_1$–$C_6$alkoxy; or $R_2$ is phenyl($C_0$–$C_2$alkyl) or heteroaryl($C_0$–$C_2$alkyl), each of which is substituted with 0 to 3 substituents independently chosen from
(i) hydroxy, halogen, nitro, cyano, amino, sulfonamide, —CHO, $C_1$–$C_6$haloalkyl, and $C_1$–$C_6$haloalkoxy, and
(ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, heterocycloalkyl($C_0$–$C_2$alkyl), and —C(O)$R_{13}$; each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl)amino;

$Z_2$ is

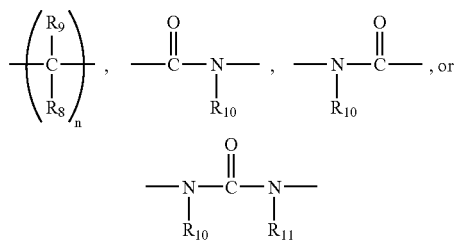

wherein
$R_8$ and $R_9$ are independently hydrogen, $C_1$–$C_6$alkyl, $C_1$–$C_6$alkoxy, or halogen; and n is 0, 1, or 2;
$R_{10}$ and $R_{11}$ are independently
(iii) hydrogen or $C_1$–$C_6$alkyl; or
(iv) phenyl or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and —C(O)$R_{13}$;

$R_3$ is hydrogen or $C_1$–$C_6$alkyl, or
$R_3$ is $C_3$–$C_7$cycloalkyl($C_0$–$C_2$alkyl), heterocycloalkyl($C_0$–$C_2$alkyl), phenyl, or heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$ alkyl), mono- and di-($C_1$–$C_6$alkyl)amino($C_1$–$C_6$alkyl), $C_2$–$C_6$alkanoyl, and —C(O)$R_{13}$; or
$R_3$ is phenoxy phenyl, each of which phenyl rings is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), $C_2$–$C_6$alkanoyl, and —C(O)$R_{13}$.

2. A compound or pharmaceutically acceptable salt thereof according to claim 1, wherein
$R_1$ is hydrogen, halogen, $C_1$–$C_7$alkyl, $C_1$–$C_6$alkoxy, $C_3$–$C_7$cycloalkyl($C_0$–$C_2$alkyl), heterocycloalkyl($C_0$–$C_2$alkyl), sulfonamide, ($C_1$–$C_6$alkoxy)$C_1$–$C_6$alkyl, ($C_1$–$C_6$alkoxy)$C_1$–$C_6$alkoxy, mono- or di-($C_1$–$C_6$alkyl)amino, or mono- or di-($C_1$–$C_6$alkyl)amino($C_1$–$C_6$alkyl); or
$R_1$ is phenyl substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl;

W is phenyl or a 5- or 6-membered heteroaryl ring; substituted with 0 to 3 substituents independently chosen from hydroxy, nitro, cyano, amino, sulfonamide, —CHO, halogen, oxo, $C_1$–$C_6$alkyl; $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino ($C_1$–$C_6$alkyl), and $C_2$–$C_6$alkanoyl;

X is N or CH;
$R_2$ is $C_1$–$C_7$alkyl, $C_3$–$C_7$cycloalkyl($C_0$–$C_2$alkyl), heterocycloalkyl($C_0$–$C_2$alkyl), $C_1$–$C_6$alkoxy, ($C_1$–$C_6$alkoxy)$C_1$–$C_6$alkyl, or ($C_1$–$C_6$alkoxy)$C_1$–$C_6$alkoxy; or
$R_2$ is phenyl($C_0$–$C_2$alkyl) or 5- or 6-membered heteroaryl ($C_0$–$C_2$alkyl), each of which is substituted with 0 to 3 substituents independently chosen from
(i) hydroxy, halogen, nitro, cyano, amino, sulfonamide, —CHO, $C_1$–$C_6$haloalkyl, and $C_1$–$C_6$haloalkoxy, and
(ii) $C_1$–$C_6$alkyl, $C_2$–$C_6$alkenyl, $C_2$–$C_6$alkynyl, $C_3$–$C_7$cycloalkyl, $C_1$–$C_6$alkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), $C_2$–$C_6$alkanoyl, and heterocycloalkyl($C_0$–$C_2$alkyl); each of which (ii) is substituted with 0 to 3 substituents independently chosen from halogen, hydroxy, amino, nitro, cyano, $C_1$–$C_4$alkoxy, $C_3$–$C_7$cycloalkyl, and mono- and di-($C_1$–$C_4$alkyl)amino;

$Z_2$ is

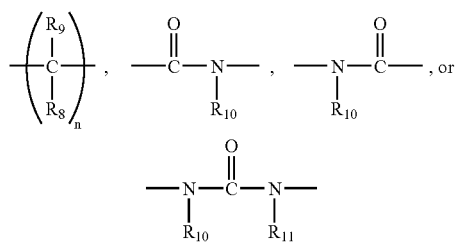

wherein $R_8$ and $R_9$ are independently hydrogen, $C_1$–$C_6$alkyl, $C_1$–$C_6$alkoxy, or halogen; and n is 0, 1, or 2;

$R_{10}$ and $R_{11}$ are independently (iii) hydrogen or $C_1$–$C_6$alkyl; or (iv) phenyl or a 5- or 6 membered heteroaryl ring, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl;

$R_3$ is hydrogen or $C_1$–$C_6$alkyl, or $R_3$ is $C_3$–$C_7$cycloalkyl($C_0$–$C_2$alkyl), heterocycloalkyl ($C_0$–$C_2$alkyl), phenyl, or a 5- or 6-membered heteroaryl, each of which is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl; or $R_3$ is phenoxy phenyl, each of which phenyl rings is substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

3. A compound or pharmaceutically acceptable salt thereof according to claim 2 wherein $R_1$ is halogen, $C_1$–$C_7$alkyl, $C_1$–$C_6$alkoxy, $C_3$–$C_7$cycloalkyl($C_0$–$C_2$alkyl), or heterocycloalkyl ($C_0$–$C_2$alkyl); or $R_1$ is phenyl substituted with 0 to 3 substituents independently chosen from hydroxy, nitro, cyano, amino, sulfonamide, —CHO, halogen, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

4. A compound or pharmaceutically acceptable salt thereof according to claim 3 wherein $R_1$ is halogen or $C_1$–$C_7$alkyl; or $R_1$ is phenyl substituted with 0 to 3 substituents independently chosen from hydroxy, nitro, cyano, amino, halogen, $C_1$–$C_6$alkyl, $C_3$–$C_7$cycloalkyl, $C_1$–$C_6$alkoxy, $C_1$–$C_2$haloalkyl, $C_1$–$C_2$haloalkoxy, and mono- and di-($C_1$–$C_4$alkyl)amino.

5. A compound or pharmaceutically acceptable salt thereof according to claim 4 wherein $R_1$ is phenyl substituted with 0 to 3 substituents independently chosen from hydroxy, nitro, cyano, amino, halogen, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl) amino.

6. A compound or pharmaceutically acceptable salt thereof according to claim 4 wherein $R_1$ is bromo or $C_1$–$C_4$alkyl; or $R_1$ is phenyl substituted with 0 to 2 substituents independently chosen from fluoro, chloro, bromo, $C_1$–$C_2$alkyl, and $C_1$–$C_2$alkoxy.

7. A compound or pharmaceutically acceptable salt thereof according to claim 6 wherein W is phenyl, pyridyl, pyrimidinyl, imidazolyl, pyrrolyl, pyrazolyl, furanyl, thienyl, oxazolyl, or isoxazolyl, each of which is substituted with 0 to 3 substituents independently chosen from hydroxy, nitro, cyano, amino, sulfonamide, —CHO, halogen, oxo, $C_1$–$C_6$alkyl, $C_2$–$C_6$alkenyl, $C_2$–$C_6$alkynyl, $C_3$–$C_7$cycloalkyl, $C_1$–$C_6$alkoxy, $C_1$–$C_6$haloalkyl, $C_1$–$C_6$haloalkoxy, ($C_1$–$C_6$alkoxy)$C_1$–$C_6$alkyl, ($C_1$–$C_6$alkoxy)$C_1$–$C_6$alkoxy, $C_1$–$C_6$alkylthio, mono- and di-($C_1$–$C_6$alkyl)amino, amino($C_1$–$C_6$alkyl), mono- and di-($C_1$–$C_6$alkyl)amino($C_1$–$C_6$alkyl), and $C_2$–$C_6$alkanoyl.

8. A compound or pharmaceutically acceptable salt thereof according to claim 7 wherein W is phenyl, pyridyl, pyrimidinyl, imidazolyl, pyrrolyl, pyrazolyl, furanyl, thienyl, oxazolyl, or isoxazolyl, each of which is substituted with 0 to 3 substituents independently chosen from hydroxy, nitro, cyano, amino, halogen, oxo, $C_1$–$C_4$alkyl, $C_1$–$C_4$alkoxy, $C_1$–$C_2$haloalkyl, $C_1$–$C_2$haloalkoxy, and mono- and di-($C_1$–$C_4$alkyl)amino.

9. A compound or pharmaceutically acceptable salt thereof according to claim 8, wherein W is imidazolyl, pyrrolyl, or pyrazolyl, each of which is substituted with 0 to 3 substituents independently chosen from hydroxy, cyano, halogen, oxo, $C_1$–$C_4$alkyl, $C_1$–$C_4$alkoxy, trifluoromethyl, and trifluoromethoxy.

10. A compound or pharmaceutically acceptable salt thereof according to claim 6 of Formula 2

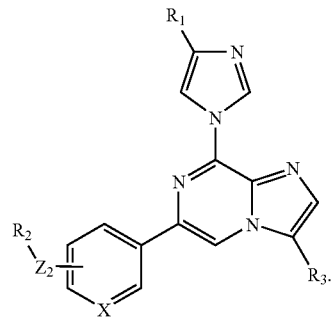

(Formula 2)

11. A compound or pharmaceutically acceptable salt thereof according to claim 6 of Formula 3

(Formula 3)

12. A compound or pharmaceutically acceptable salt thereof according to claim 6 of Formula 4:

(Formula 4)

13. A compound or pharmaceutically acceptable salt thereof according to claim 11, wherein X is N.

14. A compound or pharmaceutically acceptable salt thereof according to claim 11, wherein X is CH.

15. A compound or pharmaceutically acceptable salt thereof according to claim 9 wherein $Z_2$ is wherein
  $R_8$ and $R_9$ are independently hydrogen or $C_1$–$C_6$alkyl; and n is 0, 1, or 2; and
  $R_{10}$ and $R_{11}$ are independently hydrogen, $C_1$–$C_6$alkyl, or phenyl.

16. A compound or pharmaceutically acceptable salt thereof according to claim 15, wherein $Z_2$ is wherein, $R_{10}$ and $R_{11}$ are independently hydrogen, methyl, or ethyl.

17. A compound or pharmaceutically acceptable salt thereof according to claim 16 wherein $R_{10}$ and $R_{11}$ are both hydrogen.

18. A compound or pharmaceutically acceptable salt thereof according to claim 9 of Formula 6

(Formula 6)

19. A compound or pharmaceutically acceptable salt thereof according to claim 9 of Formula 7

(Formula 7)

20. A compound or pharmaceutically acceptable salt thereof according to claim 9 of Formula 8

(Formula 8)

21. A compound or pharmaceutically acceptable salt thereof according to claim 19 wherein $R_2$ is phenyl, pyridyl, pyrimidinyl, pyrazinyl, imidazolyl, pyrrolyl, furanyl, thienyl, oxazolyl, or isoxazolyl, each of which may be either directly attached or bound via a C$_1$–C$_2$alkyl linker, and each of which is substituted with 0 to 3 substituents independently chosen from:

(i) hydroxy, halogen, nitro, cyano, amino, sulfonamide, —CHO, C$_1$–C$_6$haloalkyl, and C$_1$–C$_6$haloalkoxy, and (ii) C$_1$–C$_6$alkyl, C$_2$–C$_6$alkenyl, C$_2$–C$_6$alkynyl, C$_3$–C$_7$cycloalkyl, C$_1$–C$_6$alkoxy, (C$_1$–C$_6$alkoxy)C$_1$–C$_6$alkyl, (C$_1$–C$_6$alkoxy)C$_1$–C$_6$alkoxy, C$_1$–C$_6$alkylthio, mono- and di-(C$_1$–C$_6$alkyl)amino, amino(C$_1$–C$_6$alkyl), mono- and di-(C$_1$–C$_6$alkyl)amino(C$_1$–C$_6$alkyl), C$_2$–C$_6$alkanoyl, and heterocycloalkyl(C$_0$–C$_2$alkyl); each of which (ii) is substituted with 0 to 3 substituents independently chosen from halogen, hydroxy, amino, nitro, cyano, C$_1$–C$_4$alkoxy, C$_3$–C$_7$cycloalkyl, and mono- and di-(C$_1$–C$_4$alkyl)amino.

22. A compound or pharmaceutically acceptable salt thereof according to claim 21, wherein R$_2$ is phenyl(C$_0$–C$_2$alkyl), pyridyl(C$_0$–C$_2$alkyl), or pyrimidinyl(C$_0$–C$_2$alkyl), each of which is substituted with 0 to 3 substituents independently chosen from:

(i) hydroxy, halogen, nitro, cyano, amino, C$_1$–C$_2$haloalkyl, and C$_1$–C$_2$haloalkoxy, and (ii) C$_1$–C$_6$alkyl, C$_3$–C$_7$cycloalkyl, C$_1$–C$_6$alkoxy, (C$_1$–C$_6$alkoxy)C$_1$C$_6$alkyl, C$_1$–C$_4$alkylthio, mono- and di-(C$_1$–C$_4$alkyl)amino, mono- and di-(C$_1$–C$_4$alkyl)amino(C$_1$–C$_4$alkyl), and heterocycloalkyl(C$_0$–C$_2$alkyl); each of which (ii) is substituted with 0 to 3 substituents independently chosen from halogen, hydroxy, amino, nitro, cyano, C$_1$–C$_4$alkoxy, C$_3$–C$_7$cycloalkyl, and mono- and di-(C$_1$–C$_4$alkyl)amino.

23. A compound or a pharmaceutically acceptable salt thereof according to claim 22, wherein R$_2$ is phenyl or benzyl, each of which is substituted with 0 to 3 substituents independently chosen from halogen, hydroxy, amino, C$_1$–C$_4$alkyl, C$_1$–C$_4$alkoxy, C$_1$–C$_4$alkylthio, C$_1$–C$_2$haloalkyl, and C$_1$–C$_2$haloalkoxy.

24. A compound or pharmaceutically acceptable salt thereof according to claim 23, wherein R$_3$ is hydrogen or C$_1$–C$_6$alkyl, or R$_3$ is C$_3$–C$_7$cycloalkyl, (C$_3$–C$_7$cycloalkyl)methyl, heterocycloalkyl, (heterocycloalkyl)C$_1$–C$_2$alkyl, phenyl, phenyl, pyridyl, pyrimidinyl, pyrazinyl, imidazolyl, pyrrolyl, furanyl, thienyl, oxazolyl, or isoxazolyl, each of which is substituted with 0 to 3 substituents independently chosen from hydroxy, nitro, cyano, amino, halogen, C$_1$–C$_6$alkyl, C$_3$–C$_7$cycloalkyl, C$_1$–C$_6$alkoxy, C$_1$–C$_2$haloalkyl, C$_1$–C$_2$haloalkoxy, and mono- and di-(C$_1$–C$_4$alkyl)amino; or R$_3$ is phenoxyphenyl, each of which phenyl rings is substituted with 0 to 3 substituents independently chosen from hydroxy, nitro, cyano, amino, halogen, C$_1$–C$_6$alkyl, C$_3$–C$_7$cycloalkyl, C$_1$–C$_6$alkoxy, C$_1$–C$_2$haloalkyl, C$_1$–C$_2$haloalkoxy, and mono- and di-(C$_1$–C$_4$alkyl)amino.

25. A compound or pharmaceutically acceptable salt thereof according to claim 24, wherein R$_3$ is hydrogen, C$_1$–C$_6$alkyl, C$_3$–C$_7$cycloalkyl (C$_0$–C$_1$alkyl), phenyl, or phenoxyphenyl.

26. A compound or pharmaceutically acceptable salt thereof according to claim 25, wherein R$_3$ is hydrogen or C$_1$–C$_4$alkyl.

27. A compound or pharmaceutically acceptable salt thereof according to claim 1 of Formula 9

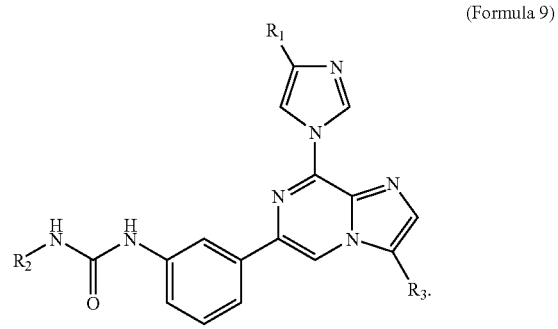

(Formula 9)

28. A compound or pharmaceutically acceptable salt thereof according to claim 1 of Formula 10

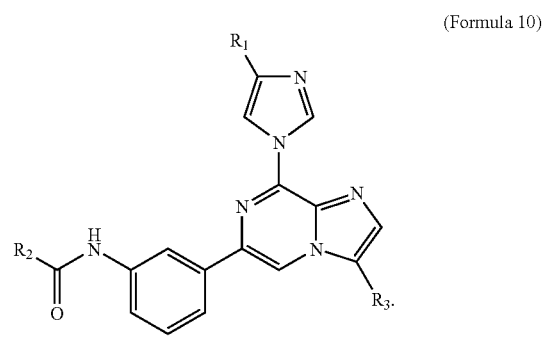

(Formula 10)

29. A compound or pharmaceutically acceptable salt thereof according to claim 1 of Formula 11

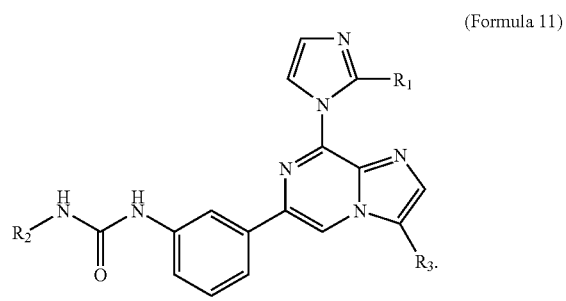

(Formula 11)

30. A compound or pharmaceutically acceptable salt thereof according to claim 1 of Formula 12

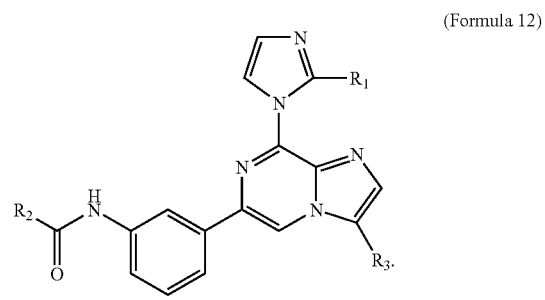

(Formula 12)

31. A compound or pharmaceutically acceptable salt thereof according to claim 1 of Formula 13

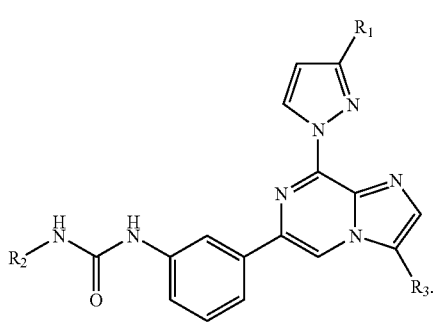

(Formula 13)

32. A compound or pharmaceutically acceptable salt thereof according to claim 1 of Formula 14

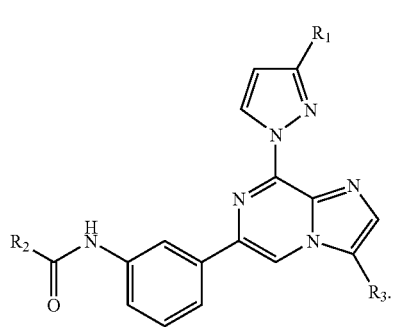

(Formula 14)

33. A compound or pharmaceutically acceptable salt thereof according to claim 30, wherein
   $R_1$ is bromo or $C_1$–$C_4$alkyl; or
   $R_1$ is phenyl substituted with 0 to 2 substituents independently chosen from fluoro, chloro, bromo, $C_1$–$C_2$alkyl, and $C_1$–$C_2$alkoxy;
   $R_2$ is phenyl or benzyl, each of which is substituted with 0 to 3 substituents independently chosen from:
      (i) hydroxy, halogen, amino, $C_1$–$C_2$haloalkyl, and $C_1$–$C_2$haloalkoxy, and
      (ii) $C_1$–$C_6$alkyl, $C_1$–$C_6$alkoxy, mono- and di-($C_1$–$C_4$alkyl)amino, mono- and di-($C_1$–$C_4$alkyl) amino($C_1$–$C_4$alkyl), piperazinyl($C_0$–$C_1$alkyl), piperidinyl($C_0$–$C_1$alkyl), and morpholinyl($C_0$–$C_1$alkyl); each of which (ii) is substituted with 0 to 3 substituents independently chosen from halogen, hydroxy, amino, $C_1$–$C_2$alkoxy, and mono- and di-($C_1$–$C_4$alkyl)amino; and
   $R_3$ is hydrogen or $C_1$–$C_4$alkyl.

34. A compound or pharmaceutically acceptable salt thereof according to claim 1, wherein the compound exhibits an $IC_{50}$ of 25 micromolar or less in an in vitro assay of tumor cell proliferation.

35. A compound or pharmaceutically acceptable salt thereof according to claim 1, wherein the compound exhibits an $IC_{50}$ of 10 micromolar or less in an in vitro assay of tumor cell proliferation.

36. A compound or pharmaceutically acceptable salt thereof according to claim 1, wherein the compound is:
   1-{3-[8-(4-Phenyl-imidazol-1-yl)-imidazo[1,2-a]pyrazin-6-yl]-phenyl}-3-o-tolyl-urea;
   1-(4-Chloro-phenyl)-3-{3-[8-(4-phenyl-imidazol-1-yl)-imidazo[1,2-a]pyrazin-6-yl]-phenyl}-urea;
   1-(2-Methylsulfanyl-phenyl)-3-{3-[8-(2-phenyl-imidazol-1-yl)-imidazo[1,2-a]pyrazin-6-yl]-phenyl}-urea;
   1-{3-[8-(2-Phenyl-imidazol-1-yl)-imidazo[1,2-a]pyrazin-6-yl]-phenyl}-3-o-tolyl-urea;
   1-(4-Chloro-phenyl)-3-(3-{8-[4-4chloro-phenyl)-imidazol-1-yl]-imidazo[1,2-a]pyrazin-6-yl}-phenyl)-urea;
   1-(3-{8-[4-(4-Chloro-phenyl)-imidazol-1-yl]-imidazo[1,2-a]pyrazin-6-yl}-phenyl)-3-o-tolyl-urea;
   1-(4-Chloro-phenyl)-3-{3-[8-(4-p-tolyl-imidazol-1-yl)-imidazo[1,2-a]pyrazin-6-yl]-phenyl}-urea;
   1-o-Tolyl-3-{3-[8-(4-p-tolyl-imidazol-1-yl)-imidazo[1,2-a]pyrazin-6-yl]-phenyl}-urea;
   1-(4-Chloro-phenyl)-3-{3-[8-(4-methyl-imidazol-1-yl)-imidazo[1,2-a]pyrazin-6-yl]-phenyl}-urea;
   1-(3-Chloro-4-fluoro-phenyl)-3-(3-{8-[4-(4-chloro-phenyl)-imidazol-1-yl]-imidazo[1,2-a]pyrazin-6-yl}-phenyl)-urea;
   1-(3-Chloro-4-fluoro-phenyl)-3-{3-[8-(4-phenyl-imidazol-1-yl)-imidazo[1,2-a]pyrazin-6-yl]-phenyl}-urea;
   1-(3-{8-[4-(4-Chloro-phenyl)-imidazol-1-yl]-imidazo[1,2-a]pyrazin-6-yl}-phenyl)-3-[4-(4-methyl-piperazin-1-ylmethyl)-phenyl]-urea;
   1-(3-{8-[4-(4-Chloro-phenyl)-imidazol-1-yl]-imidazo[1,2-a]pyrazin-6-yl}-phenyl)-3-(4-morpholin-4-ylmethyl-phenyl)-urea;
   1-(3-{8-[4-(4-Chloro-phenyl)-imidazol-1-yl]-imidazo[1,2-a]pyrazin-6-yl}-phenyl)-3-{4-[(3-ethoxy-propylamino)-methyl]-phenyl}-urea;
   1-(4-Chloro-phenyl)-3-{3-[8-(3-phenyl-pyrazol-1-yl)-imidazo[1,2-a]pyrazin-6-yl]-phenyl}-urea;
   1-(3-Chloro-4-fluoro-phenyl)-3-{3-[8-(3-phenyl-pyrazol-1-yl)-imidazo[1,2-a]pyrazin-6-yl]-phenyl}-urea;
   1-(3-Chloro-4-fluoro-phenyl)-3-{3-[8-(2-phenyl-imidazol-1-yl)-imidazo[1,2-a]pyrazin-6-yl]-phenyl}-urea;
   4-Chloro-N-{3-[8-(2-phenyl-imidazol-1-yl)-imidazo[1,2-a]pyrazin-6-yl]-phenyl}-benzamide;
   3-Morpholin-4-ylmethyl-N-{3-[8-(2-phenyl-imidazol-1-yl)-imidazo[1,2-a]pyrazin-6-yl]-phenyl}-benzamide;
   4-Morpholin-4-ylmethyl-N-{3-[8-(2-phenyl-imidazol-1-yl)-imidazo[1,2-a]pyrazin-6-yl]-phenyl}-benzamide;
   1-(3-Chloro-4-fluoro-phenyl)-3-{3-[8-(2-p-tolyl-imidazol-1-yl)-imidazo[1,2-a]pyrazin-6-yl]-phenyl}-urea;
   1-{3-[8-(2-p-Tolyl-imidazol-1-yl)-imidazo[1,2-a]pyrazin-6yl]-phenyl}-3-(3-trifluoromethyl-phenyl)-urea;
   1-(4-Morpholin-4-ylmethyl-phenyl)-3-{3-[8-(2-phenyl-imidazol-1-yl)-imidazo[1,2-a]pyrazin-6-yl]-phenyl}-urea;
   6-(4-Morpholin-4-ylmethyl-phenyl)-8-(2-phenyl-imidazol-1-yl)-imidazo[1,2-a]pyrazine;
   1-(4-Chloro-phenyl)-3-{3-[8-(2-o-tolyl-imidazol-1-yl)-imidazo[1,2-a]pyrazin-6-yl]-phenyl}-urea;
   1-(3-Chloro-4-fluoro-phenyl)-3-{3-[8-(2-o-tolyl-imidazol-1-yl)-imidazo[1,2-a]pyrazin-6-yl]-phenyl}-urea;
   1-(4-Chloro-phenyl)-3-(3-{8-[2-(2-methoxy-phenyl)-imidazol-1-yl]-imidazo[1,2-a]pyrazin-6-yl}-phenyl)-urea;
   1-(4-Chloro-phenyl)-3-(3-{8-[2-(2-fluoro-phenyl)-imidazol-1-yl]-imidazo[1,2-a]pyrazin-6-yl}-phenyl)-urea;
   1-(3-Chloro-4-fluoro-phenyl)-3-(3-{8-[2-(2-fluoro-phenyl)-imidazol-1-yl]-imidazo[1,2-a]pyrazin-6-yl}-phenyl)-urea;
   1-(3-{8-[2-(2-Fluoro-phenyl)-imidazol-1-yl]-imidazo[1,2-a]pyrazin-6-yl}-phenyl)-3-(3-trifluoromethyl-phenyl)-urea;

1-(3-{8-[2-(2Methoxy-phenyl)-imidazol-1-yl]-imidazo[1,2-a]pyrazin-6-yl}-phenyl)-3-(3-trifluoromethyl-phenyl)-urea;

1-(4-Chloro-phenyl)-3-{3-[8-(2-isopropyl-imidazol-1-yl)-imidazo[1,2-a]pyrazin-6-yl]-phenyl}-urea;

1-(3-Chloro-4-fluoro-phenyl)-3-{3-[8-(2-isopropyl-imidazol-1-yl)-imidazo[1,2-a]pyrazin-6-yl]-phenyl}-urea;

1-{3-[8-(4-Bromo-imidazol-1-yl)-imidazo[1,2-a]pyrazin-6-yl]-phenyl}-3-(4-chloro-phenyl)-urea;

4-Fluoro-N-{3-[8-(2-phenyl-imidazol-1-yl)-imidazo[1,2-a]pyrazin-6-yl]-phenyl}-benzamide;

3-Methoxy-N-{3-[8-(2-phenyl-imidazol-1-yl)-imidazo[1,2-a]pyrazin-6-yl]-phenyl}-benzamide 3-Methoxy-4-methyl-N-{3-[8-(2-phenyl-imidazol-1-yl)-imidazo[1,2-a]pyrazin-6-yl]-phenyl}-benzamide;

N-{3-[8-(2-Phenyl-imidazol-1-yl)-imidazo[1,2-a]pyrazin-6-yl]-phenyl}-benzamide;

2,6-Dimethyl-N-{3-[8-(2-phenyl-imidazol-1-yl)-imidazo[1,2-a]pyrazin-6-yl]-phenyl}-benzamide;

4-Fluoro-N-{3-[8-(2-p-tolyl-imidazol-1-yl)-imidazo[1,2-a]pyrazin-6-yl]-phenyl}-benzamide;

3-Methoxy-N-{3-[8-(2-p-tolyl-imidazol-1-yl)-imidazo[1,2-a]pyrazin-6-yl]-phenyl}-benzamide;

3-Methoxy-4-methyl-N-{3-[8-(2-p-tolyl-imidazol-1-yl)-imidazo[1,2-a]pyrazin-6-yl]-phenyl}-benzamide;

2-(4-Chloro-phenyl)-N-{3-[8-(2-phenyl-imidazol-1-yl)-imidazo[1,2-a]pyrazin-6-yl]-phenyl}-acetamide;

2-(4-Chloro-phenyl)-N-(3-{8-[2-(4-chloro-phenyl)-imidazol-1-yl]-imidazo[1,2-a]pyrazin-6-yl}-phenyl)-acetamide;

N-(3-{8-[2-(4-Chloro-phenyl)-imidazol-1-yl]-imidazo[1,2-a]pyrazin-6-yl}-phenyl)-2-(3-trifluoromethyl-phenyl)-acetamide;

1-(3-{8-[2-(4-Chloro-phenyl)-imidazol-1-yl]-imidazo[1,2-a]pyrazin-6-yl}-phenyl)-3-(4-morpholin-4-ylmethyl-phenyl)-urea;

1-(4-Chloro-benzyl)-3-(3-{8-[2-(4chloro-phenyl)-imidazol-1-yl]-imidazo[1,2-a]pyrazin-6-yl}-phenyl)-urea; or 1-(3-{8-[2-(4-Chloro-phenyl)-imidazol-1-yl]-imidazo[1,2-a]pyrazin-6-yl}-phenyl)-3-[4-(4-methyl-piperazin-1-ylmethyl)-phenyl]-urea.

37. A pharmaceutical composition, comprising a compound or pharmaceutically acceptable salt thereof according to claim 1, together with at least one pharmaceutically acceptable carrier or excipient.

38. A pharmaceutical composition according to claim 37, wherein the composition is formulated as an injectable fluid, an aerosol, a cream, a gel, a tablet, a capsule, a syrup, ophthalmic solution, or a transdermal patch.

39. A method for modulating binding of ATP to Hsp90 complex in vitro, the method comprising contacting cells expressing Hsp90 complex with a compound according to claim 1 or pharmaceutically acceptable salt thereof in an amount sufficient to detectably decrease the level of an Hsp90 substrate protein in vitro.

40. A method for modulating the activity of Hsp90 complex, the method comprising contacting cells expressing Hsp90 complex with a compound according to claim 1 or pharmaceutically acceptable salt thereof in an amount sufficient to detectably decrease the level of an Hsp90 substrate protein in vitro.

41. The method of claim 40 wherein the substrate protein is ErbB2, Akt, or Raf.

* * * * *